(12) United States Patent
Shin et al.

(10) Patent No.: US 10,295,885 B2
(45) Date of Patent: May 21, 2019

(54) WIDEBAND ULTRA-HIGH REFRACTIVE INDEX MESOSCOPIC CRYSTAL STRUCTURE USING SPACE-FILLING OF ELECTRIC DIPOLE AND OPTICAL DEVICE USING THE SAME

(71) Applicant: KOREA ADVANCED INSTITUTE OF SCIENCE AND TECHNOLOGY, Daejeon (KR)

(72) Inventors: Jonghwa Shin, Daejeon (KR); Yong-Hee Lee, Daejeon (KR); Tae Yong Chang, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 15/927,601

(22) Filed: Mar. 21, 2018

(65) Prior Publication Data
US 2018/0275486 A1    Sep. 27, 2018

Related U.S. Application Data

(63) Continuation of application No. PCT/KR2016/010539, filed on Sep. 21, 2016.

(30) Foreign Application Priority Data

Sep. 21, 2015  (KR) .................. 10-2015-0132969
Oct. 30, 2015  (KR) .................. 10-2015-0151969
Aug. 29, 2016  (KR) .................. 10-2016-0109940

(51) Int. Cl.
*G02F 1/355*   (2006.01)
*H01L 21/027*  (2006.01)
(Continued)

(52) U.S. Cl.
CPC ........... *G02F 1/3551* (2013.01); *G01N 21/41* (2013.01); *G01N 33/53* (2013.01); *G02B 1/02* (2013.01);
(Continued)

(58) Field of Classification Search
CPC .... G02F 1/0126; G02F 1/3515; G02F 1/3551; G02B 1/02; G02B 3/0087; G02B 5/18; G01N 21/41; G01N 33/53
See application file for complete search history.

(56) References Cited

U.S. PATENT DOCUMENTS 9,057,697 B2 *   6/2015  Amako ............... G01N 21/554
2009/0323014 A1  12/2009 Cunningham et al.
(Continued)

FOREIGN PATENT DOCUMENTS

JP    2006167855 A     6/2006
KR    1020100032447 A  3/2010
WO    WO-2017052196 A1 * 3/2017 ........... H01L 21/027

OTHER PUBLICATIONS

International Search Report of PCT/KR2016/010539 dated Dec. 8, 2016.

*Primary Examiner* — Daniel Petkovsek
(74) *Attorney, Agent, or Firm* — Greer Burns & Crain, Ltd.

(57) ABSTRACT

A wideband ultra-high refractive index mesoscopic crystal structure including: a first layer with high-conductivity unit bodies arranged in a matrix form, and a low-conductivity material disposed between the high-conductivity unit bodies; a second layer with high-conductivity unit bodies arranged in a matrix form, and a low-conductivity material disposed between the high-conductivity unit bodies; a first shield layer existing between the first and second layers and made of a low-conductivity material; and a second shield layer made of a low-conductivity material disposed on a side
(Continued)

of the second layer such that the second layer is disposed between the first shield layer and the second shield layer, wherein the high-conductivity unit bodies in the first layer overlap the high-conductivity unit bodies arranged in the second layer, and wherein the first layer, the first shield layer, the second layer, and the second shield layer are sequentially stacked one or more times.

19 Claims, 28 Drawing Sheets

(51) Int. Cl.
*H01L 29/06* (2006.01)
*G01N 21/41* (2006.01)
*G01N 33/53* (2006.01)
*G02B 1/02* (2006.01)
*G02B 3/00* (2006.01)
*G02B 5/18* (2006.01)
*G02F 1/01* (2006.01)
*G02F 1/35* (2006.01)

(52) U.S. Cl.
CPC ............. *G02B 3/0087* (2013.01); *G02B 5/18* (2013.01); *G02F 1/0126* (2013.01); *G02F 1/3515* (2013.01); *H01L 21/027* (2013.01); *H01L 29/06* (2013.01); *G02F 1/3556* (2013.01); *G02F 2202/06* (2013.01); *G02F 2203/01* (2013.01); *G02F 2203/02* (2013.01)

(56) References Cited

U.S. PATENT DOCUMENTS

2010/0097610 A1  4/2010  Yamada et al.
2010/0253997 A1  10/2010  Li

\* cited by examiner

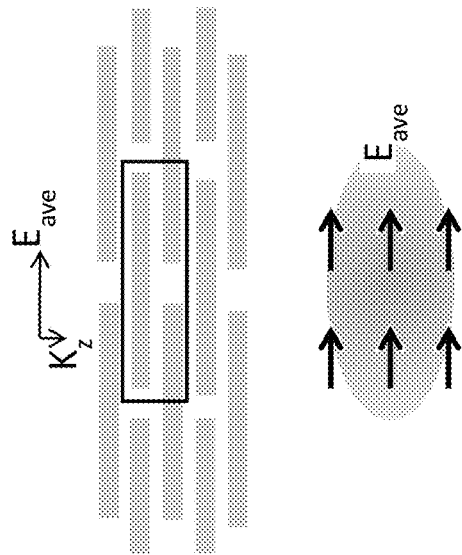
FIG. 1A
FIG. 1B
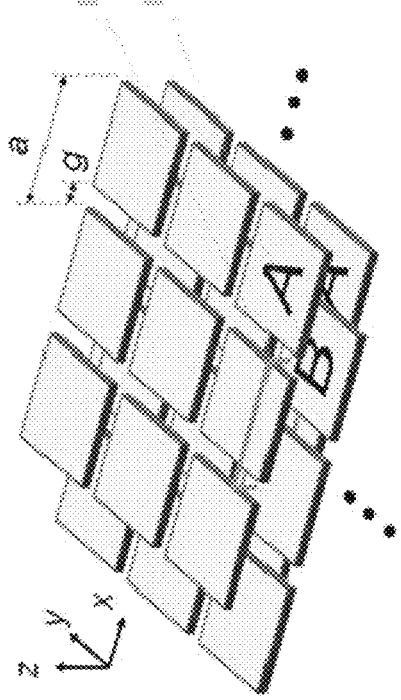
FIG. 1C
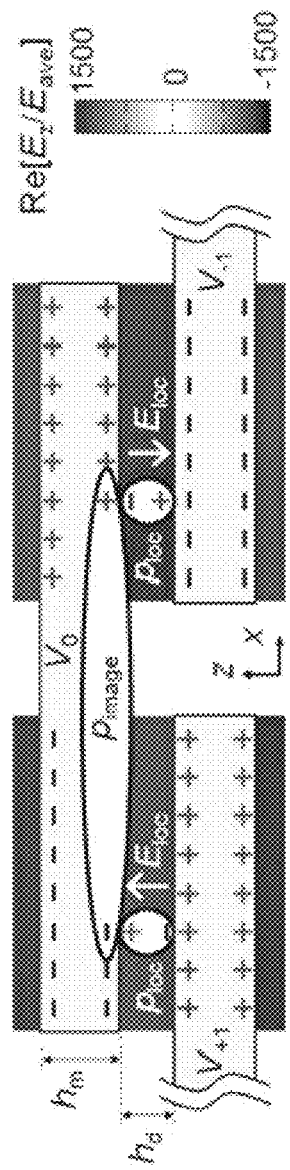

FIG. 9A
FIG. 9B
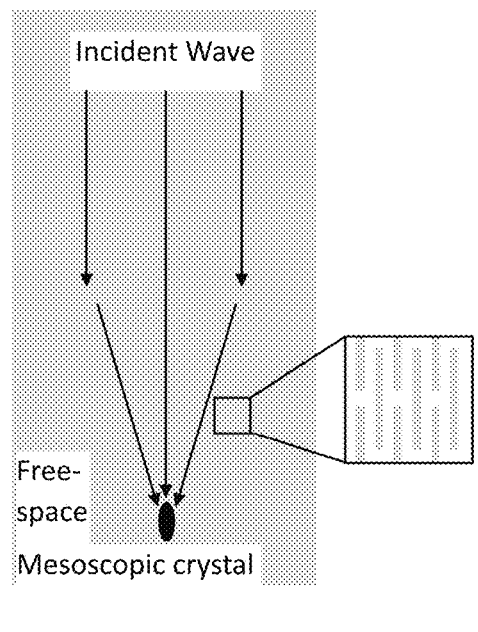
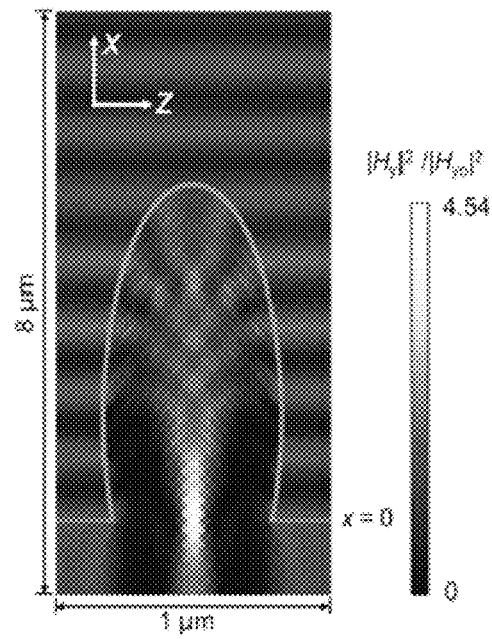
FIG. 9C
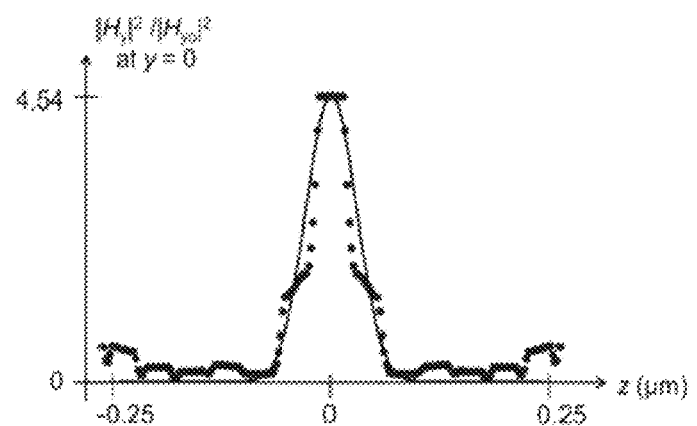

Broadband high index metamaterial $I_{int}(\omega, X) = n_{eff}^2(\omega, X) I_{ext}^{bb}(\omega)$

WIDEBAND ULTRA-HIGH REFRACTIVE INDEX MESOSCOPIC CRYSTAL STRUCTURE USING SPACE-FILLING OF ELECTRIC DIPOLE AND OPTICAL DEVICE USING THE SAME

CROSS-REFERENCE TO RELATED APPLICATIONS

This application is a continuation of PCT Application No. PCT/KR2016/010539 filed on Sep. 21, 2016, which claims priority to Korean Patent Application Number 10-2015-0132969 filed on Sep. 21, 2015; 10-2015-0151969 filed on Oct. 30, 2015; and 10-2016-0109940 filed on Aug. 29, 2016, all of which are hereby incorporated by reference in their entirety.

TECHNICAL FIELD

The present disclosure relates to a wideband high refractive index mesoscopic crystal structure based on space-filling of an electric dipole.

BACKGROUND

Since the invention of optical lens, the study of optics has evolved around the refractive index, the fundamental property of all optical materials. The refractive index described by Snell's law affects propagation speed, wavelength, diffraction, energy density, and absorption and emission of light in materials. So far, experimentally realized wideband refractive indices remain below 40, even with intricately designed artificial media.

Herein, we demonstrate a measured index of 1800 or more resulting from a mesoscopic crystal with a dielectric constant of 3 million or more. This gigantic enhancement effect originates from the space-filling curve concept from mathematics. The concept is very tenacious with respect to wideband refractive index. A wideband mega-dielectric according to the present disclosure promises not only enhanced resolution in imaging and lithography and increased fundamental absorption limits in solar energy devices, but also compact, power-efficient components for optical communication and increased performance in many other applications.

There exists a fundamental upper bound on the refractive index of any natural or artificial medium with atomic scale unit cells. For non-magnetic materials, the refractive index (n) is solely determined by the dielectric constant ($\varepsilon_r$), which in turn is determined by the atomic (or molecular) polarizability and its spatial arrangement.

The volume-averaged polarizability of an ensemble of ideal two-level systems is summarized by the following Equation 1.

$$\frac{ND^2(w_t - w)}{\varepsilon_0 \hbar [(w_t - w)^2 + \gamma^2]} \qquad \text{[Equation 1]}$$

N: density of the two-level system
D: relevant transition dipole moment
$\varepsilon_0$: vacuum permittivity
$\hbar$: reduced Planck constant
$w_t$: transition frequency between two levels
w: frequency
$\gamma$: effective damping factor For low frequencies ($w \ll w_t$), the volume-averaged polarizability of an ensemble of ideal two-level systems is $$\frac{ND^2}{\varepsilon_0 \hbar w_t}.$$

For typical N and D of solids, $$\frac{ND^2}{\varepsilon_0 \hbar w_t}$$

is on the order of unity, which is why the refractive indices of materials remain also on the order of unity. If one can increase this factor by six orders of magnitude, the dielectric constant would increase by the same amount and the refractive index, by three orders. Existing approaches to increase the refractive index are divided into resonant and non-resonant routes. The resonant schemes aim to minimize the factor in the denominator, $w_t - w$, by working near a resonance ($w_t \approx w$), using an atomic transition level or an electromagnetic resonance of artificially designed sub-wavelength structures (meta-atoms). In actual systems, the dielectric constant does not diverge on resonance due to various resonance broadening mechanisms that make $\gamma$ a non-zero value.

As one minimizes these broadening factors, the resulting index becomes larger at the design frequency; but at the same time, it becomes more frequency-dispersive and the index deviates severely even for slightly different frequencies. This makes propagation of a temporal pulse impossible without distortion. This narrowband nature and enhancement-bandwidth trade-off is an intrinsic property of resonance-based designs and presents a fundamental hurdle for practical implementations of those schemes. On the other hand, there was a proposal to increase the index based on quasi-static boundary conditions, which are free from this trade-off relationship and can provide nearly frequency-independent enhancement over a broad bandwidth. In the proposed classical model, the enhancement can be shown to increase to an arbitrarily large value if the spatial gap between metallic inclusions is reduced. However, the experimentally measured values remained below 40 as several practical and theoretical constraints impose upper bounds on the enhancement. These constraints include such as lateral fabrication resolution, dielectric breakdown, and more fundamentally, the breakdown of classical material models at sub-nanometer size gaps. Hence, a vitally different approach is required to enhance the refractive index much beyond the current record.

DISCLOSURE OF THE INVENTION

Problems to be Solved by the Invention

According to the present disclosure, there is provided a mesoscopic crystal having an experimentally verified mega-dielectric constant. An experimentally measured refractive index thereof is 1800 and a dielectric constant thereof is $3.3 \times 10^6$. The principle is based on quasi-static boundary conditions and space-filling geometries that are inherently frequency independent. The experimental results show excellent agreement with theoretical and numerical predictions.

Means for Solving the Problems

An aspect of the present disclosure provides a wideband ultra-high refractive index mesoscopic crystal structure using space-filling of an electric dipole, including: a first layer in which a plurality of high-conductivity unit bodies is arranged in a matrix form, and a low-conductivity material is disposed between the high-conductivity unit bodies to insulate the high-conductivity unit bodies from each other; a second layer in which a plurality of high-conductivity unit bodies is arranged in a matrix form, and a low-conductivity material is disposed between the high-conductivity unit bodies to insulate the high-conductivity unit bodies from each other, the second layer being adjacent to the first layer; and a shield layer existing between the first and second layers and made of a low-conductivity material, wherein the high-conductivity unit bodies in the first layer overlap the plurality of high-conductivity unit bodies arranged in the second layer, and a stack in which the first layer, the shield layer, the second layer, and the shield layer are sequentially stacked is repeated one or more times.

Another aspect of the present disclosure provides a non-linear optical device including: a mesoscopic crystal structure; a third layer; and a fourth layer, wherein the mesoscopic crystal structure includes: a first layer in which a plurality of high-conductivity unit bodies is arranged in a matrix form, and a low-conductivity material is disposed between the high-conductivity unit bodies to insulate the high-conductivity unit bodies from each other; a second layer in which a plurality of high-conductivity unit bodies is arranged in a matrix form, and a low-conductivity material is disposed between the high-conductivity unit bodies to insulate the high-conductivity unit bodies from each other, the second layer being adjacent to the first layer; and a shield layer existing between the first and second layers and made of a low-conductivity material, and wherein the high-conductivity unit bodies in the first layer overlap the plurality of high-conductivity unit bodies arranged in the second layer, a stack in which the first layer, the shield layer, the second layer, and the shield layer are sequentially stacked is repeated one or more times, and the mesoscopic crystal structure exists between the third layer and the fourth layer.

The present disclosure provides an optical modulator including: a wideband ultra-high refractive index mesoscopic crystal structure, wherein the mesoscopic crystal structure includes: a first layer in which a plurality of high-conductivity unit bodies is arranged in a matrix form, and a low-conductivity material, is disposed between the high-conductivity unit bodies to insulate the high-conductivity unit bodies from each other; a second layer in which a plurality of high-conductivity unit bodies is arranged in a matrix form, and a low-conductivity material is disposed between the high-conductivity unit bodies to insulate the high-conductivity unit bodies from each other, the second layer being adjacent to the first layer; and a shield layer existing between the first and second layers and made of a low-conductivity material, and wherein, the high-conductivity unit bodies in the first layer overlap the plurality of high-conductivity unit bodies arranged in the second layer, a stack in which the first layer, the shield layer, the second layer, and the shield layer are sequentially stacked is repeated one or more times, and at least one of the first layer, the shield layer, and the second layer has optical nonlinearity; and the optical modulator operates using a refractive index that varies depending on an intensity of an electromagnetic field applied thereto.

Effects of the Invention

A wideband mega-dielectric medium according to the present disclosure promises not only enhanced resolution in imaging and lithography and increased fundamental absorption limits in solar energy devices, but also compact, power-efficient components for optical communication and increased performance in many other applications.

BRIEF DESCRIPTION OF THE DRAWINGS

FIG. 1A is a schematic diagram of a wideband ultra-high refractive index mesoscopic crystal structure using space-filling of an electric dipole according to the present disclosure.

FIG. 1B illustrates a unit cell shown in FIG. 1A in a vertical cut plane and indicates the direction of an electric field of a polarized electromagnetic wave in the unit cell.

FIG. 1C illustrates an electric dipole in a unit cell induced by a given electric field $E_{ave}$.

FIG. 2A shows space-filling curves of a mesoscopic crystal according to the present disclosure.

FIG. 2B shows space-filling curves of a mesoscopic crystal in which metallic plates are straightly aligned.

FIG. 2C shows an effective dielectric constant compared to vacuum permittivity according to FIG. 2A and FIG. 2B.

FIG. 4A shows the magnitude and phase of a reflection coefficient, FIG. 4B shows the magnitude and phase of a transmission coefficient, FIG. 4C shows the complex relative permittivity assuming the mesoscopic crystal structure is a non-magnetic material and without any assumption, FIG. 4D shows the complex relative permeability, and FIG. 4E shows the refractive index and FOM assuming the mesoscopic crystal structure is a non-magnetic material and without any assumption.

FIGS. 9A-9C are provided to explain sub-wavelength focusing with a mesoscopic crystal structure according to the present disclosure. FIG. 9A is a schematic diagram of a convex lens for sub-wavelength focusing. FIG. 9B is a magnetic field intensity profile from a 2-dimensional FDTD simulation for sub-wavelength focusing with the mesoscopic crystal structure according to the present disclosure. FIG. 9C is provided to explain a process of obtaining a half-width of wavelength focusing.

BEST MODE FOR CARRYING OUT THE INVENTION

Figure 2A:
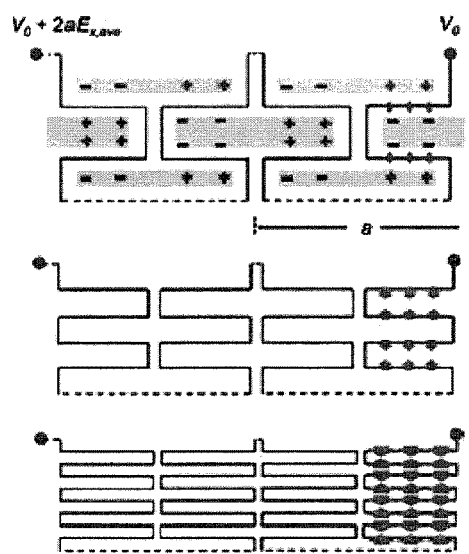
FIGS. 2A-2C show space-filling curves corresponding to mesoscopic crystals.

The advantages and characteristics of the present disclosure and a method of achieving the advantages and characteristics will be clear by referring to exemplary embodiments described below in detail together with the accompanying drawings. However, the present disclosure is not limited to exemplary embodiment disclosed herein but will be implemented in various forms. The exemplary embodiments are provided by way of example only so that a person with ordinary skill in the art can fully understand the disclosures of the present disclosure and the scope of the present disclosure. Therefore, the present disclosure will be defined only by the scope of the appended claims. The terms used herein are provided only for illustration of the exemplary embodiments but not intended to limit the present disclosure. As used herein, the singular terms include the plural reference unless the context clearly indicates otherwise. The terms "comprises" and/or "comprising" specify the presence of stated components, steps, operations, and/or elements, but do not preclude the presence or addition of one or more other components, steps, operations, and/or elements.

Hereinafter, exemplary embodiments of the present disclosure will be described in detail with reference to the accompanying drawings.

FIG. 1A is a schematic diagram of a wideband ultra-high refractive index mesoscopic crystal structure using space-filling of an electric dipole according to the present disclosure, FIG. 1B illustrates a unit cell shown in FIG. 1A in a vertical cut plane and indicates the direction of an electric field of a polarized electromagnetic wave in the unit cell, and FIG. 1C illustrates an electric dipole in a unit cell induced by a given electric field $E_{ave}$.

The mega-dielectric mesoscopic crystal illustrated in FIG. 1A shows a structure of the proposed mesoscopic crystal. Electrically insulated metal plate layers A and B are stacked in A-l-B-l fashion with insulating layers l, and the metal layers are overlapped by a half-unit cell. An insulating dielectric host is not shown for clarity and fills the entire space between metals. A rectangle shown in FIG. 1B indicates a single unit cell cross section. The mesoscopic structure (upper figure) is considered as an effective, homogeneous medium, and, thus, it can be assumed that $E_{ave}$ is uniform under quasi-static assumption (lower figure). In FIG. 1C, the electric field profile in a single unit cell cross section was obtained from FEM simulations (using a=750 μm, g=100 μm, $h_m$=400 nm, and $h_d$=300 nm as parameters of the mesoscopic crystal structure). It is assumed that copper is embedded in silica host. The enhanced z directional electric field inside the dielectric layer gives a several orders-of-magnitude increased dipole moment (small vertical ellipse). The image dipole inside the metal is further enhanced (large horizontal ellipse). Consequently, geometrically enhanced, space-filled local dipoles result in enormous homogenized polarization.

In some examples, the wideband ultra-high refractive index mesoscopic crystal structure includes a metal, a carbon compound, and a doped semiconductor material. The metal may include at least one of Al, Ag, Au, Pt, Pd, Cu, Zn, Ti, Fe, Cr, Ni, Mg, Na, K, Ir, Os, W, and Re. The carbon compound may be graphene. The doped semiconductor material may include indium tin oxide (ITO) and indium zinc oxide (IZO).

In some examples, a dielectric material may include an oxide and a nitride as a material having a dielectric constant with a negative real part, or a semiconductor material and a polymer having a low filling density, and the oxide may include at least one of silicon dioxide ($SiO_2$), aluminum oxide (III) ($Al_2O_3$), and silver oxide (II) (AgO), and the nitride may include silicon tetranitride, and the dielectric material may be composed of a combination of the oxide, the nitride, the semiconductor material, and the polymer.

Figure 2B:
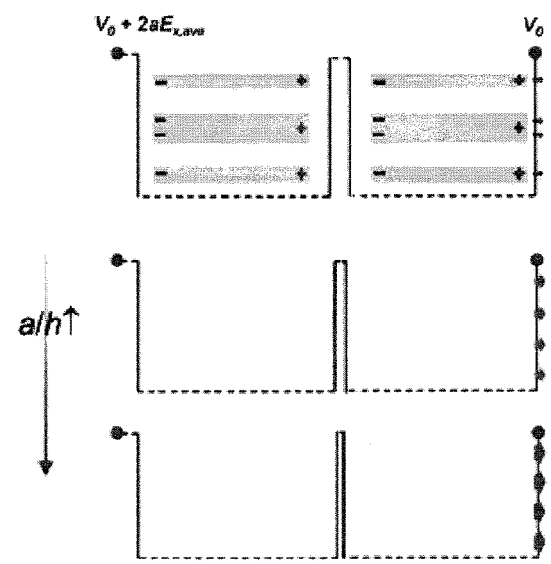
Figure 2C:
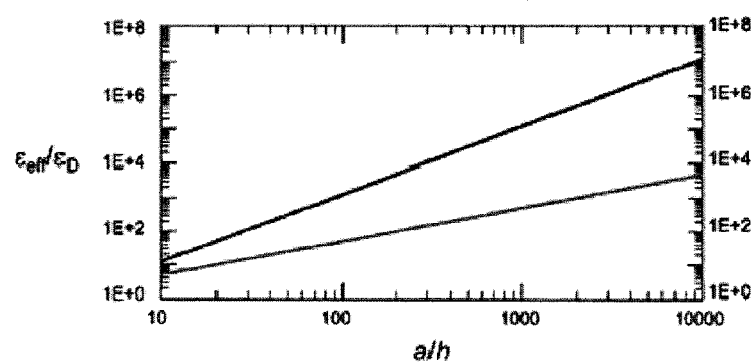

FIGS. 2A-2C show space-filling curves corresponding to mesoscopic crystals. FIG. 2A shows space-filling curves of a mesoscopic crystal according to the present disclosure, FIG. 2B shows space-filling curves of a mesoscopic crystal in which metallic plates are straightly aligned, and FIG. 2C shows an effective dielectric constant compared to vacuum permittivity according to FIG. 2A and FIG. 2B.

FIG. 2A shows 2-dimensional space-filling curves of the proposed structure for various aspect ratios. The space-filling curve follows the dielectric host between metals. As the aspect ratio, a/h, increases, the total length of the space-filling curve across a unit volume between two dots (indicated by $V_0+2aE_{x,ave}$ and $V_0$, respectively) increases linearly. Further, the arrow on the right represents a local dipole moment and it can be intuitively seen that the local dipole moment per unit length of the space-filling curve increases linearly. This is indicated by longer black solid line and thicker arrow along with the increase in aspect ratio (a/h). FIG. 2B shows space-filling curves of a straightly aligned metal plate structure for various aspect ratios. Although the dipole moment density along the curve increases in the case where the aspect ratio increases, the total length of the space-filling curve remains constant when the aspect ratio increases. In this case, the space-filling curve does not fill the space differently from FIG. 2A. FIG. 2C shows a function of the aspect ratio (a/h) at logarithmic scale and the dielectric constant enhancement factor ($\varepsilon_{eff}/\varepsilon_D$) for the structure shown in FIG. 2A and the structure shown in FIG. 2B. The dielectric constant enhancement factor increases in proportion to the square of the aspect ratio in the case of FIG. 2A but shows a linear relationship with the aspect ratio in the case of FIG. 2B depending on an array of metal plates.

The wideband mega-dielectric crystal according to the present disclosure is based on a space-filling geometry. FIG. 1A shows a structure diagram of the proposed composite material. The key concept of the present disclosure is that layers A and B in which thin and wide metallic plates are repeatedly arranged are stacked together with insulating dielectric spacer layers l in an alternating manner and overall in an A-l-B-l fashion, and the layers A and B are arranged such that an apex of the metal plate in the layer A is in the vicinity of the center of the metal plate in the layer B in a plane view. The vicinity of the center of the metal plate in the layer B is determined by a value g shown in FIG. 1A. That is, the metal plates in the layers A and B are shifted with respect to each other by a half unit cell in both lateral directions, forming a body-centered tetragonal crystal. The unit cell size should be much smaller than the wavelength if the crystal is to be considered an effective, homogeneous medium. The plate thickness is chosen to be smaller than the skin depth for wideband operation. There are many possible choices of plate shapes and lateral array configurations, such as a triangular plate or a hexagonal plate (FIGS. 15A and 15B), in addition to the square plates in a square lattice considered here. The principle of dielectric constant enhancement can be understood in terms of the enhancement of effective polarization density for a given macroscopic electric field.

For the conceptual explanation, we make several assumptions for simplicity, some of which will later be relaxed in our rigorous analytic model. First, we assume an x-polarized macroscopic plane wave propagating in a z-direction inside an infinite crystal (FIG. 1A and FIG. 1B). We focus on a mesoscopic region composed of several unit cells of the crystal, which is still much smaller than the wavelength, and assume that the macroscopic electric field $E_{ave}$ is uniform in this region (narrow region) (FIG. 1B). Due to the smallness of the unit cell size a (a<λ/40, where Δ is the wavelength of interest) and the plate thickness ($h_m$<skin depth), we calculate the field and charge distribution within a unit cell under the quasi-static (irrotational electric field) approximation. We neglect the electric field inside the metal (consider only charge distribution on the metal), assuming that the permittivity of metal is high enough in magnitude. We further assume that the structure is uniform in a y-direction (i.e., infinitely-long metallic strips instead of finite metallic plates), which is a good approximation if the lateral separation between plates is very small (g<<a). Under these conditions, each metal strip has a spatially-constant electric potential, indicated as $V_n$ in FIG. 1C. Because the adjacent upper and lower metal strips are displaced by a/2 in an x-direction, their (adjacent upper and lower metal strips') potential difference is simply $\Delta V = V_{+1} - V_0 = V_0 - V_{-1} = (a/2) \cdot E_{ave}$. In this case, the displacement in the z-direction $h_d + h_m$ does not contribute to $\Delta V$ because $E_{ave}$ is in the x-direction (perpendicular to the z-direction). Now, the mechanism of the dielectric constant can be understood directly from the local electric field distributions. As the metal strip surfaces are equi-potential surfaces, the local electric fields are perpendicular to the surfaces. Furthermore, the local electric fields, when integrated along the z-direction between two opposing surfaces of strips, should be consistent regardless of the potential difference, $\Delta V$, calculated from $E_{ave}$. That is, the localized electric fields $E_{loc}$ satisfy the following Equation 2.

$$E_{loc} = \frac{a}{2h_d} \cdot E_{ave} \qquad \text{[Equation 2]}$$

Hence, z-directional local electric fields and local dipole moments induced by these electric fields inside the filling dielectric are enhanced by a factor of $$\frac{a}{2h_d}.$$

These local induced dipole moments give rise to much larger x-directional dipole moment by a magnification factor of $$\frac{a}{2h_d}$$

due to the image charges in the metal strips illustrated in FIG. 1C. (As different metal strips are insulated from one another, the image charges have no other choice but to form dipole pairs with opposing charges inside the same metallic strip.) Finally, the volume averaged macroscopic polarization retains this $$\left(\frac{a}{2h_d}\right)^2$$

enhancement of the dipole moment. Because the local dipole moments fill the most of space except in metals with a volume fraction $$\frac{h_d}{h_m + h_d},$$

the overall enhancement factor then becomes $$\left(\frac{a}{2h_d}\right)^2 \cdot \frac{h_d}{h_m + h_d}.$$

Thus, the effective dielectric constant reflecting the enhancement factor follows Equation 3.

$$\varepsilon_{\text{eff}} = \varepsilon_d \cdot \left(\frac{a}{2h_d}\right)^2 \cdot \left(\frac{h_d}{h_m + h_d}\right) \qquad \text{[Equation 3]}$$

The quantitative values of local electric fields in FIG. 1C (see color bar scale on the right) is from the finite element method simulation (FEM) of copper strips embedded in silica, with the unit cell parameters, a=750 μm, g=100 μm, $h_d$=300 nm, $h_m$=400 nm, and wavelength $\lambda_o$=15 mm. The result shows that the above quasi-static analysis is very accurate.

One immediate observation from the derivation is that the homogenized dielectric constant is linearly proportional to $\varepsilon_d$ with a coefficient of $$\frac{a^2}{4} \cdot \frac{1}{(h_d(h_m + h_d))}.$$

This means that this mesoscopic crystal structure works as a universal dielectric constant multiplier. This is because the enhancement coefficient is solely determined by geometric parameters and is independent of $\varepsilon_d$ and frequency. This makes the enhancement inherently a very wideband phenomenon with nearly-constant enhancement from zero frequency up to the functional frequency. This statement remains true as long as quasi-static approximation is valid. The potential difference inside the metal strip is negligible. In terms of structural and material parameters, it translated to the conditions that a unit cell dimension a should be much smaller than the wavelength, and that the permittivity $\varepsilon_m$ of metal is large in magnitude, satisfying $$\frac{a}{2h_d} \ll \frac{|\varepsilon_m|}{\varepsilon_d}.$$

Because $$\frac{|\varepsilon_m|}{\varepsilon_d} \gg 1,$$

even at optical frequencies, the functional frequency can be not only radio and microwave frequencies, but also terahertz and optical frequencies. In some examples, the wavelength of an electromagnetic wave penetrating the wideband ultra-high refractive index mesoscopic crystal structure may be from 10 nm to 100 nm, but may not be limited thereto.

Further, the enhancement factor is proportional to $$\left(\frac{a}{h}\right)^2$$

(herein, h=$h_m$=$h_d$). This second-order dependence on the aspect ratio shares the same mathematical root as the special class of curves known as space-filling curves. It has been proved that a lower-dimensional object, such as a curve, can fill a higher dimensional space such as an area. This space-filling design principle was absent in previous high refractive index media, and their homogenized dielectric constants had linear rather than quadratic dependence on the aspect ratio. This reason limits the previously measured effective dielectric constants to moderate values of a few thousands, even with a very high aspect ratio near 1000. This is several orders of magnitude below the attainable dielectric constants with the mesoscopic crystals proposed in the present disclosure with a similar aspect ratio.

A sample of the mesoscopic crystal structure according to the present disclosure is fabricated by the following method.

For the X-band wavelength measurement, diced quartz pieces (about 0.5 mm thick) are used as substrate. The metal plates are deposited by DC magnetron sputtering of a copper target with an iron-nickel alloy porous metal plate (INVAR shadow mask), and the dielectric layers are deposited by RF magnetron sputtering of a silica ($SiO_2$) target. The dielectric layers are deposited without using any mask such as an alloy porous metal plate. Lateral positioning of additional metal layers is controlled by the alignment of the shadow mask. To make a stack of exactly two unit cells in the vertical direction, the bottom and uppermost metal layers have half the thickness of other metal layers. After deposition of the final metal layer, 500 nm of silica ($SiO_2$) was deposited to suppress copper oxidation.

The sample of the mesoscopic crystal structure according to the present disclosure is measured using a microwave by the following method.

An X-band waveguide (X281C, Agilent) connected with a network analyzer (8510C, Agilent) is used to measure transmission coefficients $S_{21}$ of the samples. Effective dielectric constants and refractive indices of the samples are obtained with the transfer matrix method. Before each measurement, the setup is calibrated by the standard TRL 2-port calibration method. The samples are inserted into a waveguide sample holder, and silver paste is applied to the contact boundary to suppress potential leakage of electromagnetic waves. The $S_{21}$ raw data are moving averaged using a Gaussian function with FWHM (full width at half maximum) of 0.1 GHz. The moving averaged $S_{21}$ data are used to obtain effective optical parameters, and the $S_{21}$ raw data are in FIG. 9.

Depending on the measurement result, a simulation is performed by the following method.

To calculate electric fields inside a unit cell (FIG. 1C, 5 GHz) and to obtain effective optical parameters (FIGS. 3A-3D to FIGS. 6A-6D and FIGS. 10A-10D), a finite element method (FEM) simulation tool (COMSOL Multiphysics) is utilized. The permittivity of copper is calculated from measured DC conductivity, and that of $SiO_2$ is assumed to be 3.9. The simulation is first conducted in an x-z 2-dimensional setup ignoring g in the y-direction (e.g., biaxial crystal of metal strips) which is very small compared to the wavelength. The results are converted to the uniaxial case by multiplying a relevant geometric factor. The scattering coefficients $S_{11}$ and $S_{21}$ are obtained and used to obtain both homogenized relative permittivity and permeability (FIGS. 4A-4E) with the transfer matrix method. For imaging of FIGS. 7A-7B and FIG. 8 and focusing simulations of FIGS. 9A-9C, a finite-difference time-domain simulation tool (Lumerical FDTD solution), is used to show wideband performance. For the microwave imaging simulations, it is assumed that the mesoscopic crystal has dimensional parameters of $h_d=h_m=0.4$ μm, $g=40$ μm, and $a=1200$ μm; copper and silica ($SiO_2$) are used. For the IR focusing simulations, it is assumed that the parameters are $h_d=h_m=g=10$ nm and $a=200$ nm; aluminum and a dielectric with a refractive index of 1.4 are used.

Figure 3C:
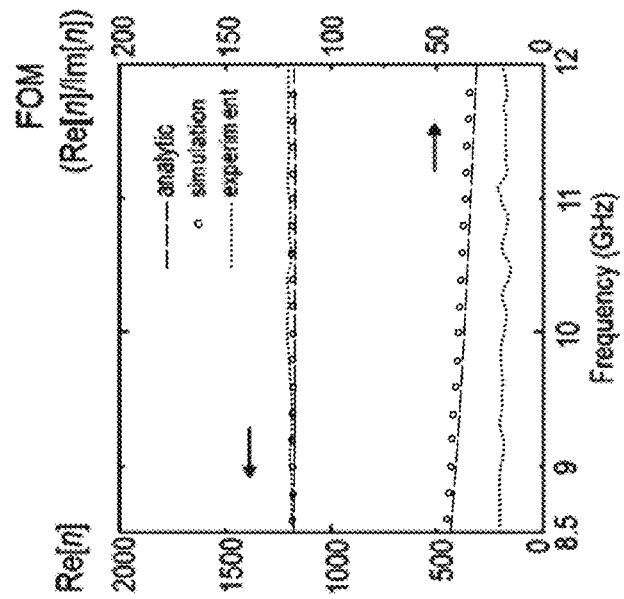
FIG. 3C shows a real part (left axis) and an imaginary part (right axis) of an effective dielectric constant of the mesoscopic crystal structure according to the present disclosure for an X-band frequency range.
Figure 3D:
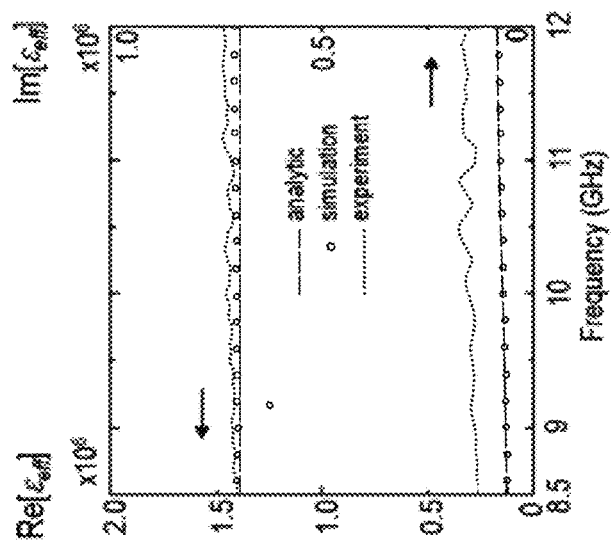
FIG. 3D shows an effective refractive index and a figure of merit (FOM).
Figure 3A:
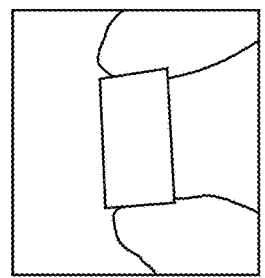
FIG. 3A shows a sample of a mesoscopic crystal structure according to the present disclosure.
Figure 3B:
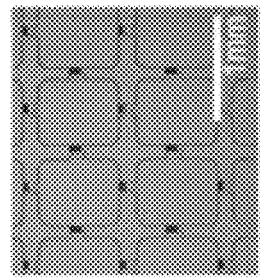
FIG. 3B shows a microstructure of the mesoscopic crystal structure according to the present disclosure.

FIG. 3A shows a macroscopic structure of a sample of a mesoscopic crystal structure according to the present disclosure, FIG. 3B shows a top view of a microstructure of the mesoscopic crystal structure according to the present disclosure, FIG. 3C shows a real part (left axis) and an imaginary part (right axis) of an effective dielectric constant $\varepsilon_{eff}$ of the mesoscopic crystal structure according to the present disclosure for an X-band frequency range, and FIG. 3D shows an effective refractive index and a figure of merit (FOM).

FIGS. 3A-3D show effective dielectric constants, effective refractive indices, and FOM values calculated by three methods, i.e., experiment, simulation, and analytic model. The mesoscopic crystal parameters include $a=750$ μm, $g=100$ μm, $h_m=400$ nm, and $h_d=300$ nm which are the same as in FIG. 1C.

It can be seen from FIGS. 3A-3D that the analytic model, simulations, and experimental data show excellent agreement for $Re[\varepsilon_{eff}]$. It can be seen from FIG. 3D that the effective refractive index is 1000 or more and the experimentally measured FOM is 15 or more for the X-band frequency range.

The analytic model is induced as follows.

The lateral dimension of the unit cell is represented as a and the metal plate and the dielectric have the thickness and permittivity of ($h_m$, $\varepsilon_m$) and ($h_d$, $\varepsilon_d$), respectively. An electric field inside a vertical dielectric gap is represented as $E_{zd}(x)$ and a horizontal factor of an electric field inside the metal is represented as $E_{xm}(x)$. Since $h_m$ and $h_d$ have small values, it is assumed that the both quantities are constants in the vertical direction within the respective regions. Under quasi-static source-free conditions, $\nabla \times E=0$, $\nabla \cdot D=0$. As long as the solenoidal nature of a D field is related to Dx and Dz fields, line integration of the E field for an arbitrary path from the center ($x=0$, $z=0$) of a plate to the center ($x=a/2$, $z=h_m+h_d$) of another plate is constant due to the irrotational nature of an E field, which satisfies the following Equation 4.

$$\begin{cases} \int_0^{x'} E_{xm}(x, \text{plate 1})dx + h_d E_{zd}(x') + \\ \int_{x'}^{\frac{a}{2}} E_{xm}(x, \text{plate 2})dx = \text{Constant} \\ \text{and} \\ \varepsilon_m \frac{dE_{xm}(x, \text{plate 1})}{dx} \cdot \frac{h_m}{2} = \varepsilon_m E_{zd}(x) \end{cases} \quad [\text{Equation 4}]$$

An Ezd field proportional to a Exdo field can be obtained using a conversion symmetry $E_{xm}(x,\text{plate 2})=E_{xm}(x-a/2, \text{plate 1})$ and a two-fold rotational symmetry from ($x=a/4$, $z=(h_d+h_m)/2$). The Exdo field refers to a dielectric field of a contact surface between the metal plate and the lateral dielectric gap.

$$E_{zd}(x) = \quad [\text{Equation 5}]$$
$$E_{xdo} \frac{g}{h_d}\left(1-\frac{\varepsilon_d}{\varepsilon_m}\right) \frac{\exp\left[P\left(x+\frac{a}{4}\right)\right]+\exp\left[-P\left(x+\frac{a}{4}\right)\right]}{(2+Pg)\exp[PL]+(2-Pg)\exp[-PL]},$$

where $$P = \sqrt{\frac{4\varepsilon_d}{\varepsilon_m h_m h_d}} \quad \text{and} \quad L = \frac{a}{4} - \frac{g}{2}$$

Likewise, $E_x(x)$ can also be obtained. The effective dielectric constant can be obtained according to Equation 6 using an averaged electric field and electric displacement inside the unit cell.

$$\varepsilon_{eff} = \frac{(\varepsilon_m h_m + \varepsilon_d h_d)Q\left(1-\frac{\varepsilon_d}{\varepsilon_m}\right)+2\varepsilon_d h_m + \varepsilon_d h_d + \frac{\varepsilon_d^2}{\varepsilon_m}h_d}{2(h_m+h_d)\left\{\frac{1}{2}\left(1-\frac{\varepsilon_d}{\varepsilon_m}\right)Q+\left(\frac{\varepsilon_d}{\varepsilon_m}-\frac{g}{a}\cdot\frac{\varepsilon_d}{\varepsilon_m}+\frac{g}{a}\right)\right\}}, \quad [\text{Equation 6}]$$

where $$Q = \frac{Pg\{\exp(PL)-\exp(-PL)\}}{(2+Pg)\exp(PL)+(2-PG)\exp(-PL)},$$

when $\varepsilon_m \to \infty$, '$\varepsilon_m Q$' converges on $$\frac{2\varepsilon_d g L}{h_m h_d}.$$

Then, with respect to $h_m$, $h_d \ll g \ll a$, $$\varepsilon_{eff} \to \varepsilon_d\left[\frac{a^2}{4(h_m+h_d)h_d}-\frac{ag}{2(h_m+h_d)h_d}+\frac{h_m a}{(h_m+h_d)g}+\frac{h_d a}{2(h_m+h_d)g}\right] \approx$$

$$\varepsilon_d = \left[\frac{a^2}{4(h_m+h_d)h_d}\right]$$

is satisfied.

However, even if $h_m$, $h_d \ll g \ll a$ is not satisfied, the analytic model can be applied using Equation 4.

The proposed structure for microwave operation around 10 GHz (FIG. 3A and FIG. 3B and methods) was fabricated. The unit cell parameters used here are the same as in FIG. 1C and the structure can be scaled down in the terahertz electromagnetic wave and visible regime. Because the geometry is simple, it is easy to adjust to different scales. The complex effective dielectric constants are obtained from scattering parameters measured using the waveguide method with a vector network analyzer. The obtained dielectric constants and refractive index are compared to quantitative theoretical predictions and to numerical simulation results. For the theoretical values, we developed an analytic model taking into account the finite and complex permittivity of metal. For the simulations, we utilized FEM analysis considering the actual permittivity of metal.

FIG. 3C and FIG. 3D reveal that measured effective dielectric constant and refractive index are in excellent agreement with both analytic and numerical predictions. It is noteworthy that the theoretical values and numerical results were obtained without any free parameter or fitting to the experimental results. The measured real part of the effective dielectric constant is $1.4 \times 10^6$ or more and the real part of the refractive index is 1200 or more. Furthermore, these values are nearly dispersionless, showing almost identical values over the entire X-band. Theoretically and numerically, this nearly-constant trend extends down to zero frequency, which is very unusual for other metamaterials. We assumed that the relative magnetic permeability ($\mu$) is 1 in the retrieval algorithm because the thickness $h_m$ of metal is less than the skin depth (500 to 600 nm for copper) at experimental frequencies. Hence, the diamagnetic behavior of metal plates is negligible. The above assumption was verified by extracting the permeability as well as the dielectric constant from the numerical simulations which were conducted without this assumption ($\mu=1$).

Figure 4A:
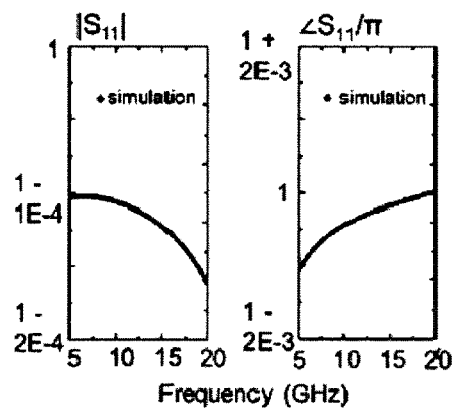
FIGS. 4A-4E are graphs provided to explain a process of obtaining the permittivity and permeability of a mesoscopic crystal structure according to the present disclosure.
Figure 4B:
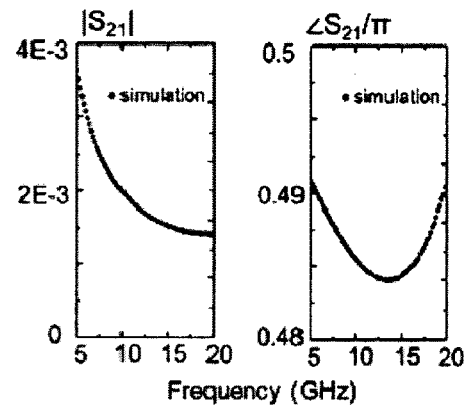
Figure 4C:
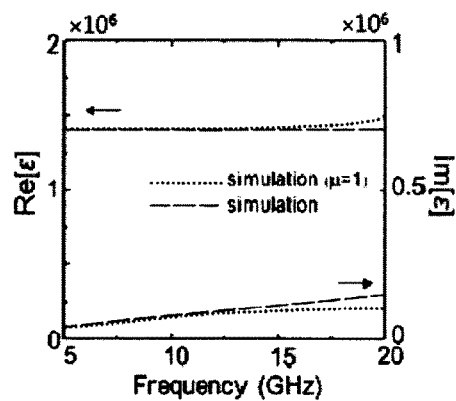
Figure 4D:
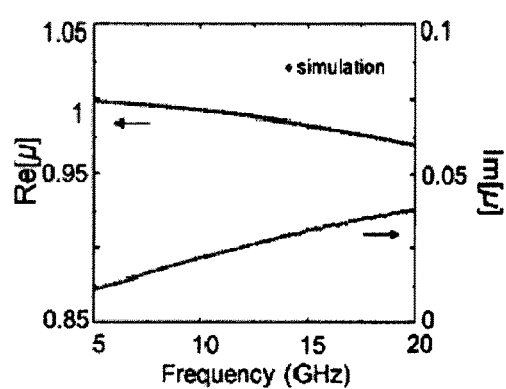
Figure 4E:
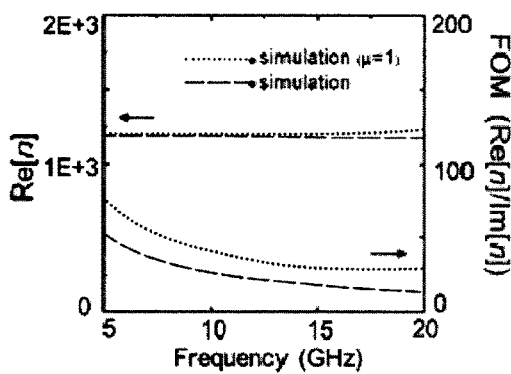

FIGS. 4A-4E are graphs provided to explain a process of obtaining the permittivity and permeability of a mesoscopic crystal structure according to the present disclosure. FIG. 4A shows the magnitude and phase of a reflection coefficient $S_{11}$, FIG. 4B shows the magnitude and phase of a transmission coefficient $S_{21}$, FIG. 4C shows the complex relative permittivity assuming the mesoscopic crystal structure is a non-magnetic material and without any assumption, FIG. 4D shows the complex relative permeability, and FIG. 4E shows the refractive index and FOM assuming the mesoscopic crystal structure is a non-magnetic material and without any assumption.

FIGS. 4A-4E show the obtained permittivity and permeability relative to the proposed mesoscopic crystal from numerical simulations. Unit cell parameters include a=750 µm, g=100 µm, $h_m$=400 nm, and $h_d$=300 nm which are the same as in FIG. 1C.

In FIG. 4C, the simulation with $\mu=1$ shows the complex relative permittivity obtained only from $S_{21}$ assuming non-magnetic material ($\mu=1$), and lower lines show the complex relative permittivity obtained from both $S_{11}$ and $S_{21}$ without any assumption. Two results are almost identical within the X-band frequency range (8.5 GHz to 12 GHz), but the graph for the case of $\mu=1$ is slightly higher around 20 GHz.

FIG. 4D shows the complex relative permeability obtained from $S_{11}$ and $S_{21}$. The obtained permeability is close to vacuum permeability within 5% difference, giving support for the non-magnetic assumption, at least for the X-band, but for higher frequencies, the thickness of the metal plates (400 nm) becomes comparable to the skin depth, and, thus, the effective permeability deviates from the vacuum permeability.

FIG. 4E shows the refractive index and FOM ($\mu=1$) only from $S_{11}$ and from both $S_{11}$, and $S_{21}$.

The $S_{11}$ and $S_{21}$ can be obtained as follows.

The magnitude of the reflection coefficient $S_{11}$ is close to 1 and a small measurement error causes an increase in standard deviation of the extracted parameters, and, thus, only $S_{21}$ is used and it is assumed that the effective permeability is vacuum permeability. A network analyzer (8510C, Agilent) equipped with an X-band waveguide (X281C, Agilent) is used to measure $S_{21}$. An incident mode for the X-band rectangular waveguide is regarded as a $TE_{10}$ mode. Therefore, a material response to electromagnetic waves depends only on $\varepsilon_{xx}$, $\mu_{yy}$, and $\mu_{zz}$. Since it is assumed that $\mu(=\mu_{yy}=\mu_{zz})=1$, the fabricated mesoscopic crystal can be considered as an effective isotropic medium with $\varepsilon_{iso}=\varepsilon_{xx}$, $\mu_{iso}=1$. In this case, the refractive index is calculated as $n=[\varepsilon_{iso} \cdot \varepsilon_{iso}]^{1/2}$. A transfer matrix for the mesoscopic crystal becomes a transfer matrix for a simple isotropic plate of an oblique incident plane wave, and, thus, the entire transfer matrix is as shown in Equation 5.

$$\begin{bmatrix} A \\ B \end{bmatrix} = \begin{bmatrix} \text{transfer matrix} \\ \text{of} \\ \text{protective layer} \end{bmatrix} \begin{bmatrix} \text{transfer matrix} \\ \text{of} \\ \text{the mesoscopic} \\ \text{crystal} \end{bmatrix} \quad \text{[Equation 7]}$$

$$\begin{bmatrix} \text{transfer matrix} \\ \text{of} \\ \text{substrate} \end{bmatrix} \begin{bmatrix} C \\ D \end{bmatrix} \text{ where, } S_{21} = \frac{C}{A}.$$

A protective layer is made of RF-sputtered $SiO_2$ having a thickness of 500 nm and a substrate is formed as diced quartz wafers having a thickness of 0.5 mm, and, thus, transfer matrix components for the mesoscopic crystal can be numerically calculated using a plane wave obliquely incident to a TE plane to calculate effective parameters. Since we assume that the protective layer and the substrate are absent, $S_{21}$ can be calculated more simply as shown in Equation 6.

$$S_{21} = \frac{1}{\cos(n_{\textit{eff}} k_0 d) - i\left(\frac{z_0^2 + z_{\textit{eff}}^2}{2 z_0 z_{\textit{eff}}}\right)\sin(n_{\textit{eff}} k_0 d)} \quad \text{[Equation 8]}$$

where $z_0$: wave impedance of vacuum $$z_{\textit{eff}} = \frac{z_0}{n_{\textit{eff}}}:$$

effective wave impedance of the mesoscopic crystal $n_{\textit{eff}}$: effective refractive index of the mesoscopic crystal $k_0$: magnitude of wave vector of incident wave in vacuum d: depth of the mesoscopic crystal Since it is assumed that the effective permeability is vacuum permeability, it can be directly compared with the experimental results, and the effective permeability can be obtained from $S_{11}$ in Equation 7.

$$S_{11} = \frac{i\left(\frac{z_1^2 - z_{eff}^2}{2z_1 z_{eff}}\right)\sin(n_{eff}k_0 d)}{\cos(n_{eff}k_0 d) - i\left(\frac{z_0^2 + z_{eff}^2}{2z_0 z_{eff}}\right)\sin(n_{eff}k_0 d)} \quad \text{[Equation 9]}$$

Figure 5:
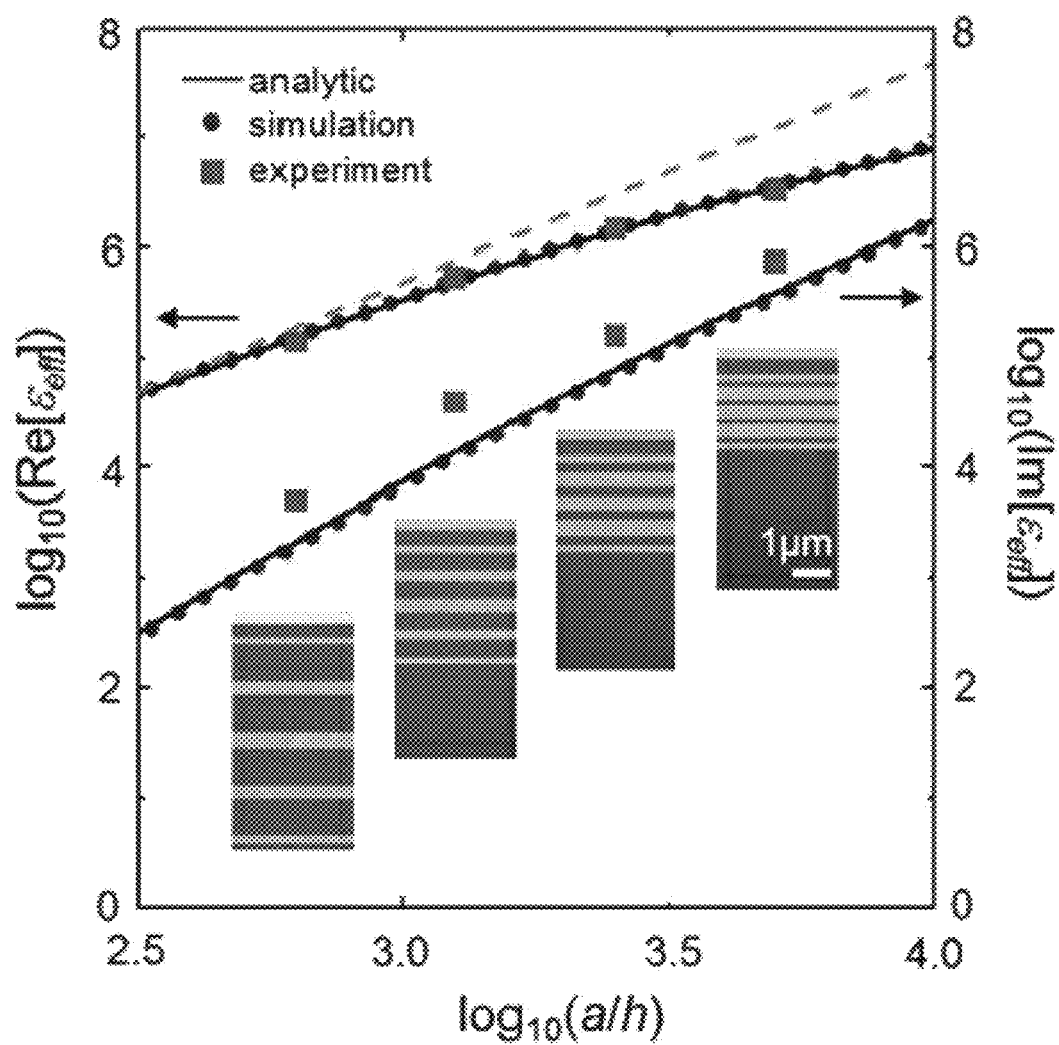
FIG. 5 shows a real part and an imaginary part of an effective dielectric constant depending on an aspect ratio (a/h).

FIG. 5 shows a real part and an imaginary part of an effective dielectric constant depending on an aspect ratio (a/h).

That is, FIG. 5 shows dielectric constants measured and obtained as a function of the aspect ratio (a/h) obtained from $S_{11}$ and $S_{21}$. The homogenized dielectric constants are plotted on a logarithmic scale at 10 GHz. The dashed line is a visual guide for the case where the effective dielectric constant has a quadratic dependence on the aspect ratio. The dielectric thickness of four fabricated samples are $h_d$=1200 nm, 600 nm, 300 nm, and 150 nm, respectively. Even for the sample with $h_d$=150 nm, $\text{Im}[\varepsilon_{eff}]$ is smaller in magnitude than $\text{Re}[\varepsilon_{eff}]$ with a refractive index of 1800 or more.

FIG. 5 shows the dependence of the measured effective dielectric constant of the proposed structure on the aspect ratio, at 10 GHz. An excellent agreement among theory, simulation, and experiment can be observed. The thickness of an insulating silica ($SiO_2$) layer is varied ($h_d$=1200 nm, 600 nm, 300 nm, or 150 nm). The other parameters are kept constant. For the moderate aspect ratios, the effective dielectric constant displays a quadratic dependence on the aspect ratio (dashed line) as predicted in the simple formulation with negligible field assumption inside metal. For the larger aspect ratios, the real part of the dielectric constants does not strictly follow quadratic dependence and the imaginary part increases. This analytically predicted and experimentally measured behaviors do not agree with each other due to non-negligible electric fields inside metal plates. For the sample with $h_d$=150 nm (a/$h_d$=5000), the measured effective dielectric constant and refractive index were $3.2 \times 10^6$ or more and 1800 or more, respectively. The experimentally measured imaginary part was larger than the analytic and numerical predictions, which is attributed to parasitic losses in the experimental setup. Still, it is much smaller than the real part, meaning that the fabricated sample has a low loss tangent. For more loss sensitive applications, a smaller aspect ratio (for example, 625) would provide FOM of 59 and a refractive index of 375. This is one order of magnitude larger than the previous wideband index record.

The principle of electric displacement manipulation with mesoscopic space-filling geometry, as well as the rigorous analytical model, can be applied to the visible regime as well. However, because of the decrease of λ and $|\varepsilon_m|$ for higher frequencies, the above-described conditions necessary for achieving dispersion-free, very high refractive index are becoming increasingly challenging to meet. A large a/h is required for high refractive index and a<<$\lambda_0$ and $$\frac{a^2}{h_d h_m} \ll \frac{|\varepsilon_m|}{\varepsilon_d},$$

needs to be satisfied. As a result, the maximum attainable refractive index has also become progressively smaller in the visible regime. FIGS. 6A-6D show record-high values of refractive index with reasonable FOM can be obtained at various frequencies.

Figure 6A:
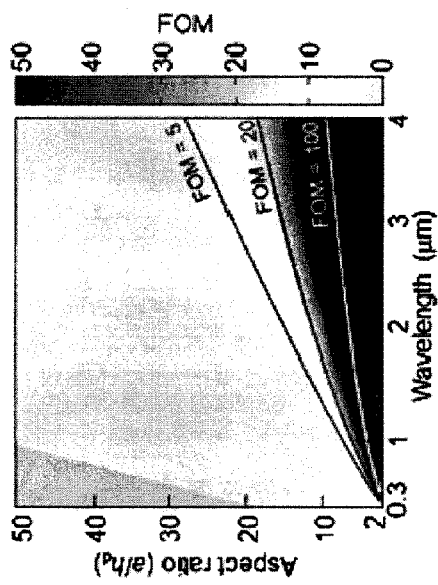
FIG. 6A shows an effective refractive index of a dielectric depending on a wavelength of a mesoscopic crystal structure according to the present disclosure.
Figure 6B:
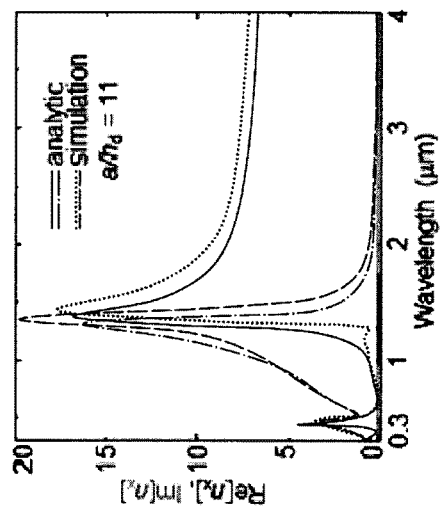
FIG. 6B shows a refractive index depending on a wavelength and an aspect ratio.
Figure 6C:
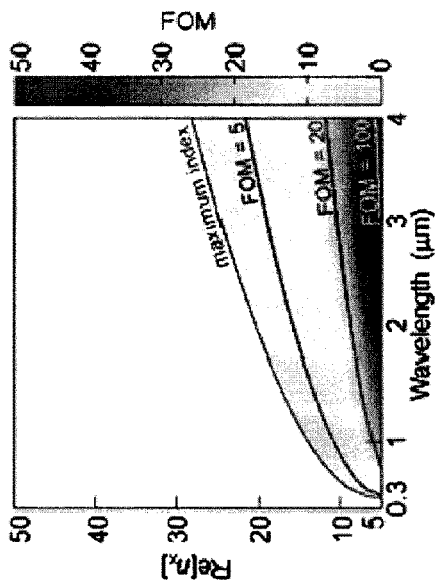
FIG. 6C shows a FOM depending on a wavelength and an aspect ratio, and FIG. 6D simultaneously shows a refractive index and a FOM depending on a wavelength by using FIG. 6B and FIG. 6C.
Figure 6D:
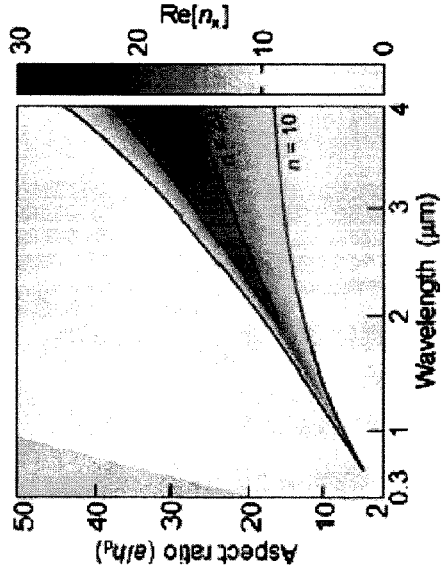

FIG. 6A shows an effective refractive index of a dielectric depending on a wavelength of a mesoscopic crystal structure according to the present disclosure, FIG. 6B shows a refractive index depending on a wavelength and an aspect ratio, FIG. 6C shows a FOM depending on a wavelength and an aspect ratio, and FIG. 6D simultaneously shows a refractive index and a FOM depending on a wavelength by using FIG. 6B and FIG. 6C.

FIGS. 6A-6D show the results of analytic model for effective refractive index of the mesoscopic crystal proposed by quasi-static approximation. FIG. 6A shows that the results of analytic model show good agreement with the refractive indices obtained from the FDTD simulations for wavelengths from 0.3 μm to 4 μm. The solid lines indicate the results of analytic model and the dashed lines indicate the results of simulation. The real part of the refractive index is 9 or more and the imaginary part is nearly 0 at 2 μm or more.

FIG. 6B and FIG. 6C show the wavelength dependent effective refractive index and FOM ($\text{Re}[n_x]/\text{Im}[n_x]$) for various aspect ratios. Grey colored area on the upper left indicates the region for a>$\lambda_0$/3; homogenization of mesoscopic crystal may not be valid within this region.

FIG. 6D shows an achievable range of an effective refractive index plotted as a function of wavelength. The maximum achievable effective index drops as the wavelength increases. However, an effective refractive index close to 15 can be obtained for a wavelength of 1.55 μm with an FOM of 5.

In plotting FIGS. 6A-6D, the known permittivity data for aluminum and the refractive index of 1.4 for the dielectric were used. The structural parameters g=$h_d$=$h_m$=5 nm were assumed, while a was varied. In FIG. 6A, as an example, the effective indices extracted from the FDTD simulations and those calculated from the analytic model were compared. In this case, wavelengths are from 0.3 μm to 5 μm for the fixed aspect ratio of 15. That is, a is 45 nm. As in the microwave calculations, the effective refractive index from the analytic model shows good agreement with the value obtained from the simulation. The real part of the refractive index is 9 or more, with low dispersion and low imaginary part for wavelengths above 2 μm. For shorter wavelengths, both the real part and the imaginary part increase, with a resonance near 1.2 μm. This frequency dispersion is observed because the criterion for the dispersion-free high index $$\frac{a^2}{h_d h_m} \ll \frac{|\varepsilon_m|}{\varepsilon_d},$$

is not fulfilled due to the smaller $|\varepsilon_m|$ for higher frequencies. If the aspect ratio is modified, a larger refractive index with smaller FOM can be obtained and a smaller refractive index with larger FOM can be obtained. FIG. 6B and FIG. 6C show the analytically calculated effective index and FOM, respectively, as functions of the wavelength and aspect ratio. It is noteworthy that there exists an upper bound on the useful aspect ratio at each frequency and that the upper bound decreases as the frequency increases. This behavior is expected because of the decreasing $|\varepsilon_m|/\varepsilon_d$. FIG. 6D is a composite graph derived from the data in FIG. 6B and FIG. 6C. FIG. 6D demonstrates the maximum value of the refractive index for a given FOM as a function of wavelength. Although the structural and material conditions for the large effective index become more stringent at shorter wavelengths, the effective index can be as high as 15 with an FOM of 5 at a wavelength of 1.55 and with realistic physical dimensions of the mesoscopic crystal. For the infrared and visible frequencies, the proposed structure, made of silver instead of aluminum, exhibits higher values of both maximum effective index and FOM because silver has a lower optical loss. However, a larger frequency dispersion can be obtained in the case of where silver is used. The high index can be used for deep-subwavelength focusing and imaging. In FDTD simulations, an optical beam with a deep subwavelength waist was found, with a full-width-at-half-maximum (FWHM) value of $\lambda_o/23.6$ at $\lambda_o=1.55$ μm upon a plane-wave illumination on a convex lens made of the mesoscopic crystal.

The proposed mesoscopic crystal made of thin, wide plates is uniaxial if the crystal has a four-fold or three-fold rotational symmetry axis perpendicular to the plane, with extreme anisotropy ($Re[\varepsilon_{x,y}]/Re[\varepsilon_z]\sim 10^5$). While it is possible to design an anisotropic version of this structure, the extreme anisotropy of the current design is naturally ideal for applications involving deep-subwavelength imaging. Furthermore, the degree of anisotropy is insusceptible to the frequency (FIGS. 7A and 7B), providing significant potential for usefulness in real applications. This is in stark contrast to previous metamaterials proposed for sub-wavelength imaging, which have very frequency dispersive equi-frequency surfaces. As a demonstration of the image transfer capability of the proposed mesoscopic crystal, finite difference time domain (FDTD) calculations are performed and FIG. 8A shows the beams from two in-phase dipole sources. The sources are separated by 30 μm which is 1/500 of a free-space wavelength at 20 GHz. The sources remain well separated after 15 mm propagation. FIG. 8B shows that the beams quickly merge into one beam after only 50 μm propagation in uniform silica ($SiO_2$). The wideband performance of the crystal was also confirmed in FIG. 7. These calculations were performed using known material parameters for copper at microwave frequencies. In FIG. 9, this principle can be observed from a scaled-down aluminum-plate array crystal in the visible regime. The aluminum-plate array crystal is shaped into a convex lens and has a FWHM of $\lambda_o/27$ at $\lambda_o=1.8$ μm.

The extreme anisotropy of the mesoscopic crystal is used to numerically demonstrate $\lambda_o/500$-feature transfer up to $\lambda_o$ length at microwave frequencies and a $\lambda_o/27$ focal spot at infrared wavelengths. The implication of wideband extreme index and dielectric constants may extend beyond pure scientific interest to deep-sub-wavelength imaging, energy applications, and other areas where the extreme optical density of states over broad frequency range is important.

Figure 7A:
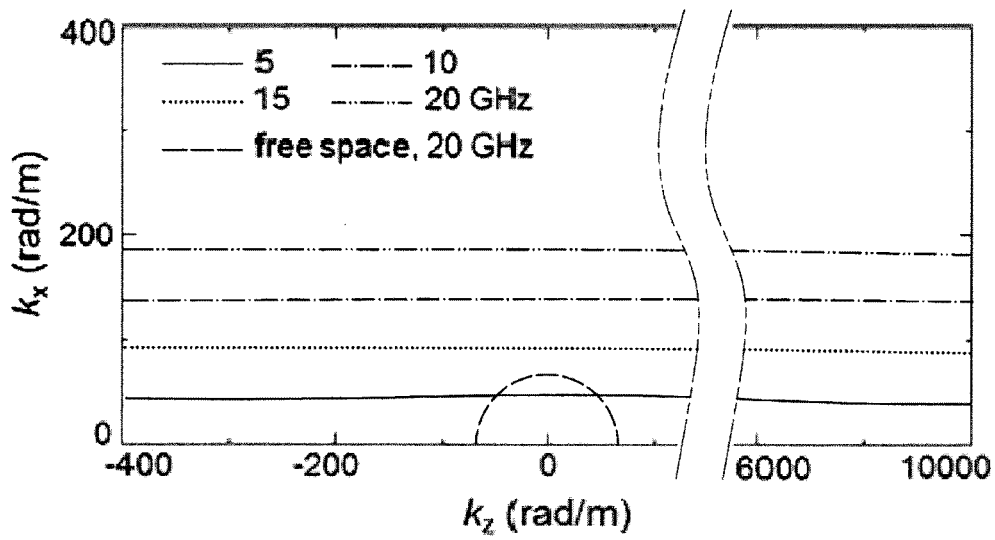
FIGS. 7A and 7B show the results of wideband subwavelength imaging performance of a mesoscopic crystal structure according to the present disclosure.
Figure 7B:
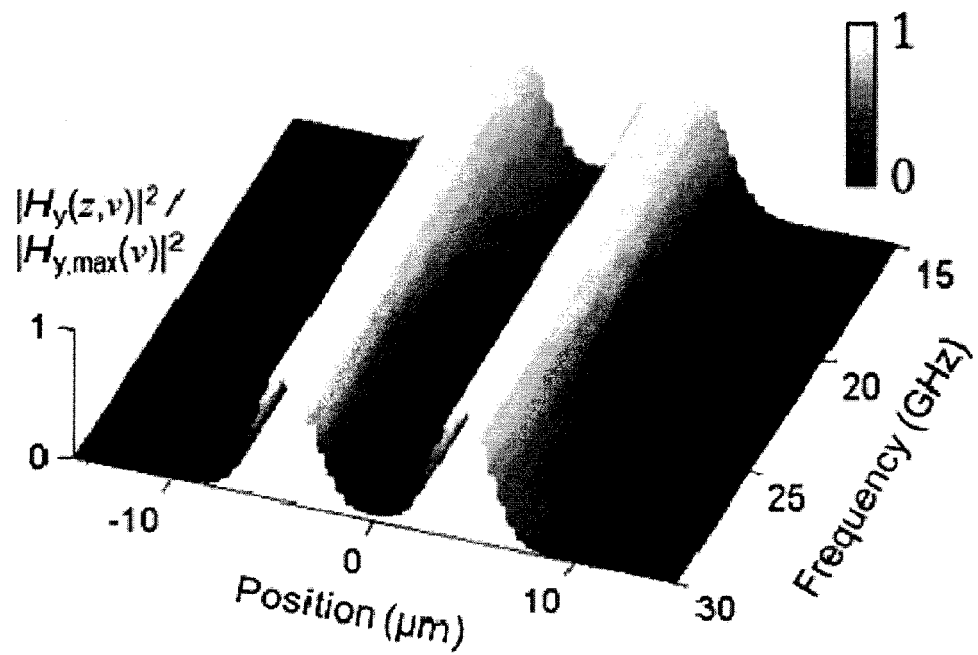

FIGS. 7A-7B show the results of wideband sub-wavelength imaging performance of a mesoscopic crystal structure according to the present disclosure.

FIGS. 7A-7B show the results of the wideband sub-wavelength imaging performance of the proposed mesoscopic crystal. FIG. 7A shows equi-frequency contours (EFC) of the proposed elliptic anisotropic crystal for various frequencies, compared to the EFC of free space (grey curve). The EFCs are almost flat over extremely large wavenumber range. The shapes of EFCs remain congruent for very broad frequency ranges, which is highly different from other elliptic or hyperbolic metamaterials. FIG. 7B shows the microwave wideband sub-wavelength imaging performance of the mesoscopic crystal for 15 GHz to 30 GHz. This is demonstrated by plotting the magnetic field intensity normalized by its maximum value at each frequency after 15 mm propagation, for two in-phase dipole sources separated by 30 μm (see FIG. 8). Similar image transfer performance is maintained over the entire frequency range.

Figure 8:
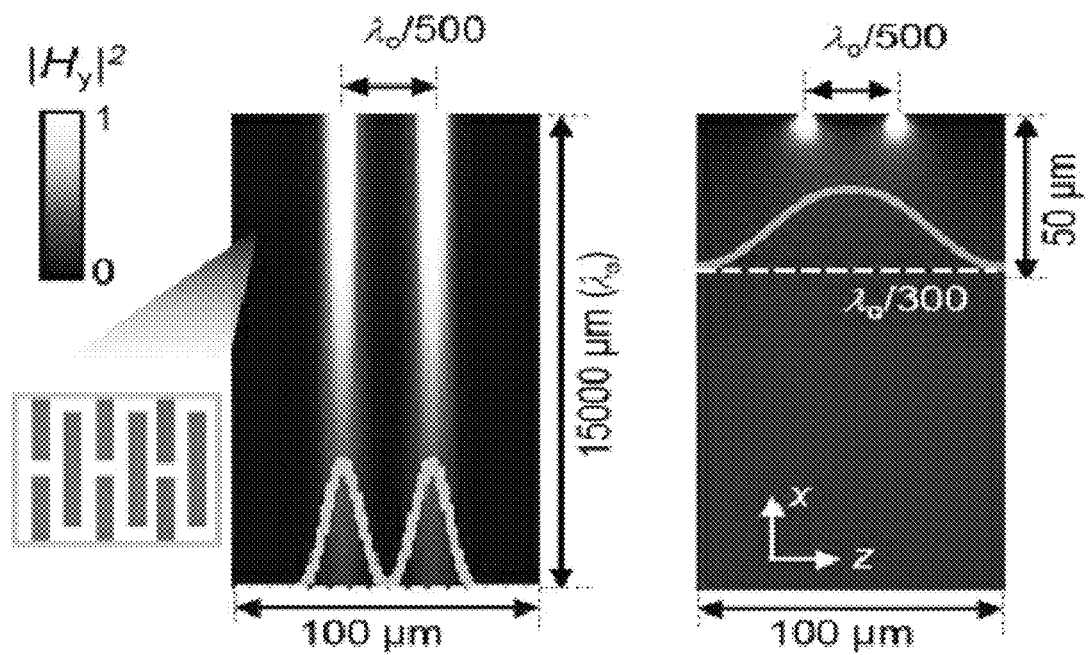
FIG. 8 shows deep sub-wavelength image transfer with an elliptic anisotropic mesoscopic crystal structure according to the present disclosure.
Figure 10A:
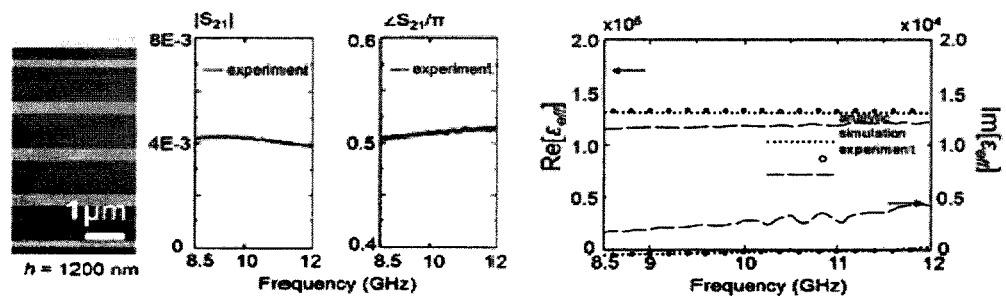
FIGS. 10A-10D show $S_{21}$ raw data and effective dielectric constants obtained from experiments, simulations, and an analytic model of each sample.
Figure 10B:
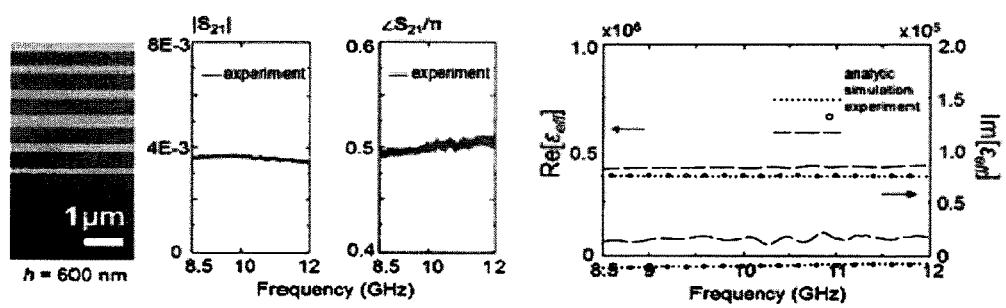
Figure 10C:
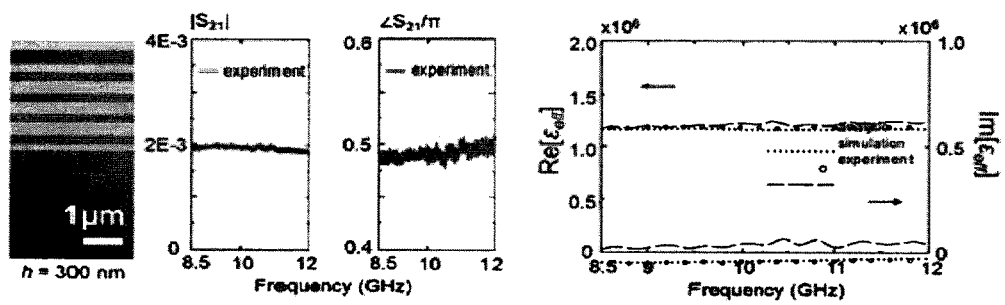
Figure 10D:
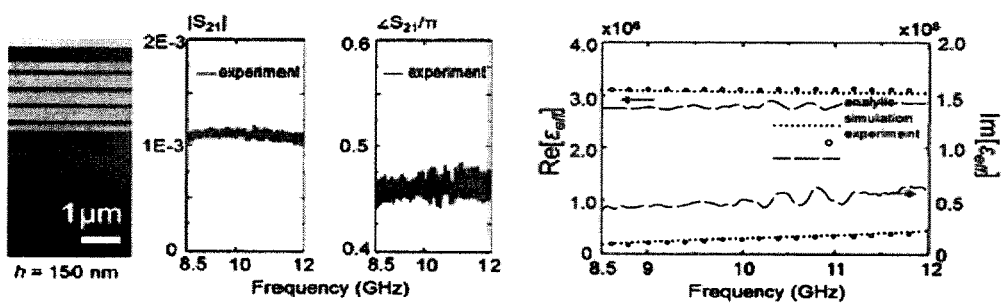

FIG. 8 shows deep sub-wavelength image transfer with an elliptic anisotropic mesoscopic crystal structure according to the present disclosure.

FIG. 8 shows deep sub-wavelength image transfer with the proposed elliptic anisotropic mesoscopic crystal. A magnetic field intensity at 20 GHz is shown. Two adjacent ($\lambda_o/500$) in-phase dipoles are observed well-separated at $1\lambda_o$ ($\lambda_o=15$ mm) (left). In contrast, a uniform dielectric ($SiO_2$) medium cannot transfer the separated image over a few tens of micrometers (right). The bright blue solid curves are the line plots of the magnetic field intensity after $1\lambda_o$ propagation as shown on the left and after $\lambda_o/300$ propagation as shown on the right.

FIGS. 9A-9C are provided to explain sub-wavelength focusing with a mesoscopic crystal structure according to the present disclosure. FIG. 9A is a schematic diagram of a convex lens for sub-wavelength focusing. FIG. 9B is a magnetic field intensity profile from a 2-dimensional FDTD simulation for sub-wavelength focusing with the mesoscopic crystal structure according to the present disclosure. FIG. 9C is provided to explain a process of obtaining a half-width of wavelength focusing.

FIGS. 9A-9C show sub-wavelength focusing with a mesoscopic crystal lens.

FIG. 9A is a schematic diagram of a convex lens made of the proposed mesoscopic crystal for subwavelength focusing. FIG. 9B is a magnetic field intensity profile normalized by the incident magnetic field intensity, from a 2-dimensional FDTD simulation. The boundary between the mesoscopic crystal and free space is indicated with a grey solid line. The incident plane wave with free space wavelength $\lambda_o$ of 1.8 μm is focused at the bottom of the mesoscopic crystal lens (x=0). From the analytic model, the effective refractive index of the mesoscopic crystal is $n_x=20$ and $n_y=2$ at $\lambda_o=1.8$ μm. FIG. 9C shows a normalized magnetic field intensity at the focal plane (blue dots) and a Gaussian fitting (black solid line) with FWHM=0.067 μm ($=\lambda_o/27$).

FIGS. 10A-10D show $S_{21}$ raw data and effective dielectric constants obtained from experiments, simulations, and an analytic model of each sample.

FIGS. 10A-10D show $S_{21}$ raw data and effective dielectric constants obtained from experiments, simulations, and an analytic model of each sample. Wideband measurement was conducted for samples with different dielectric thickness. $S_{21}$ values shown here are raw data before calculating the moving average. In order to obtain the effective dielectric constant, moving averaged $S_{21}$ values are used. Dielectric thicknesses are (a) $h_d=1200$ nm, (b) $h_d=600$ nm, (c) $h_d=300$ nm, and (d) $h_d=150$ nm. All other unit cell parameters are the same as in FIG. 1C.

Figure 11:
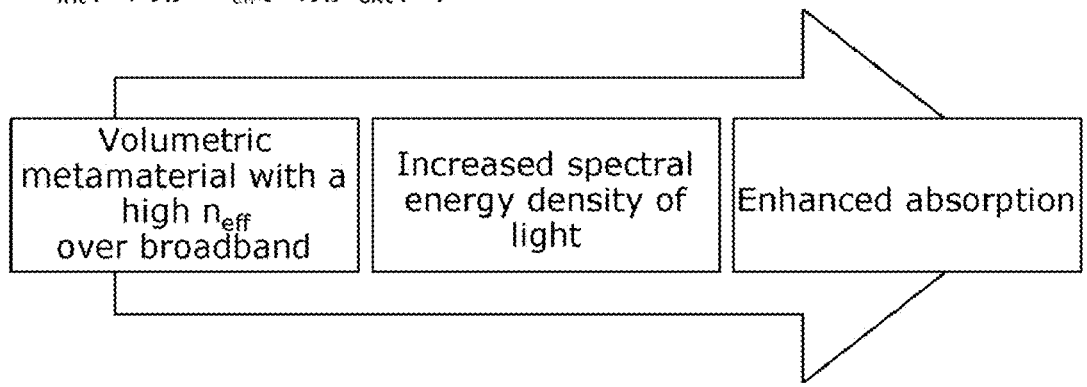
FIG. 11 shows a strategy for enhancing light absorption with a wideband high refractive index metamaterial according to an example of the present disclosure.

FIG. 11 shows a strategy for enhancing light absorption with a wideband high refractive index metamaterial according to an example of the present disclosure.

In some examples, a high-refractive index ($n_{eff}$) mesoscopic crystal structure may be used for a solar cell, but may not be limited thereto. For example, as the refractive index of the structure increases, the energy density to volume ratio of light (electromagnetic wave) increases by the square of the refractive index, and, thus, a mesoscopic crystal structure having a high refractive index of 1800 or more (microwave range) can be used for a solar cell. Therefore, the light (electromagnetic wave) absorption rate per volume increases in proportion to the energy density of light (electromagnetic wave) according to Equation 2.

$$I_{int}(w,x)=n_{eff}^2(w,x)I_{ext}^{bb}(w) \quad \text{[Equation 10]}$$

In this case, the maximum spectrum energy density of electromagnetic wave at a known temperature is proportional to the square of the refractive index (Yablonovitch limit). Therefore, if anyone can produce a material having a high effective refractive index, its energy density can increase and the electromagnetic wave absorption rate can also increase. That is, the high-refractive index mesoscopic crystal structure according to the present disclosure can be useful for a solar cell or other wavelength-energy absorbing devices. We fabricated a medium having a high effective refractive index and experimentally observed a refractive index of 1800 or more in the microwave range.

Figure 12A:
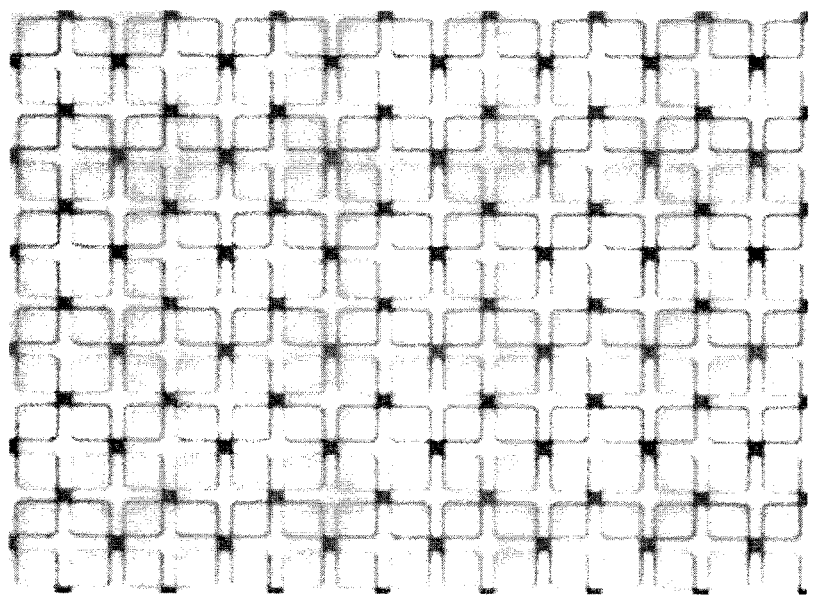
FIG. 12A is a schematic diagram of a wideband high refractive index mesoscopic crystal structure according to the present disclosure.
Figure 12B:
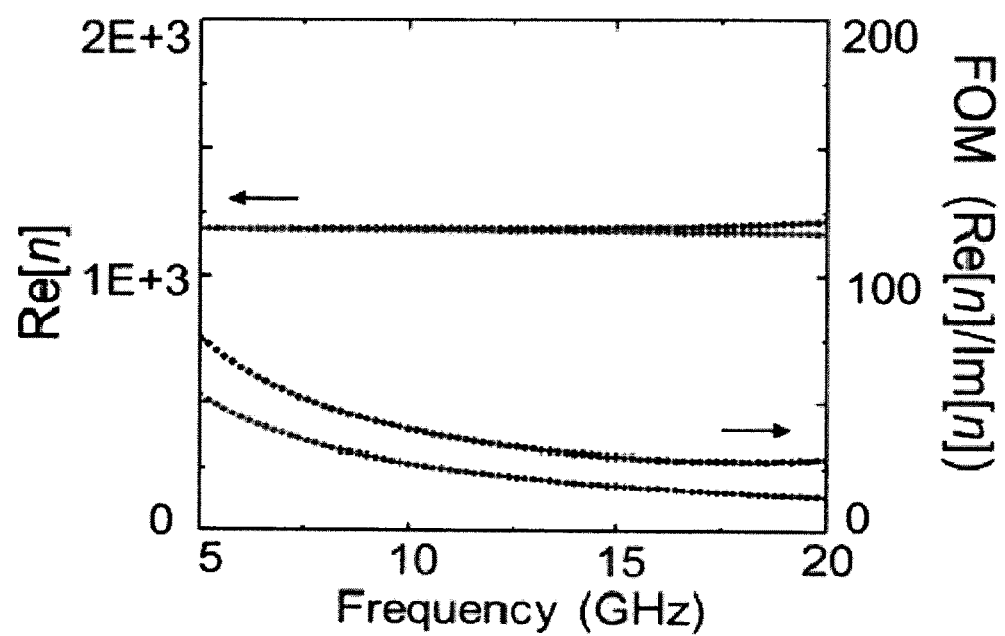
FIG. 12B shows the measured refractive index and FOM of a mesoscopic crystal according to the present disclosure.

FIG. 12A is a schematic diagram of a wideband high refractive index mesoscopic crystal structure according to the present disclosure, and FIG. 12B shows the measured refractive index and FOM of a mesoscopic crystal according to the present disclosure.

A metamaterial is shown. FIG. 12A is a structure diagram of the proposed mesoscopic crystal according to an example of the present disclosure. FIG. 12B shows the measured refractive index of the mesoscopic crystal according to an example of the present disclosure. The mesoscopic crystal according to the present example has a wideband high refractive index of 1800 or more (microwave range).

FIGS. 12A and 12B show a wideband high refractive index metamaterial. FIG. 12A is a structure diagram of the proposed mesoscopic crystal. FIG. 12B is a graph showing the measured refractive index of the mesoscopic crystal. The mesoscopic crystal according to the present disclosure exhibits a wideband high refractive index (1800 or more in the microwave range).

Figure 13:
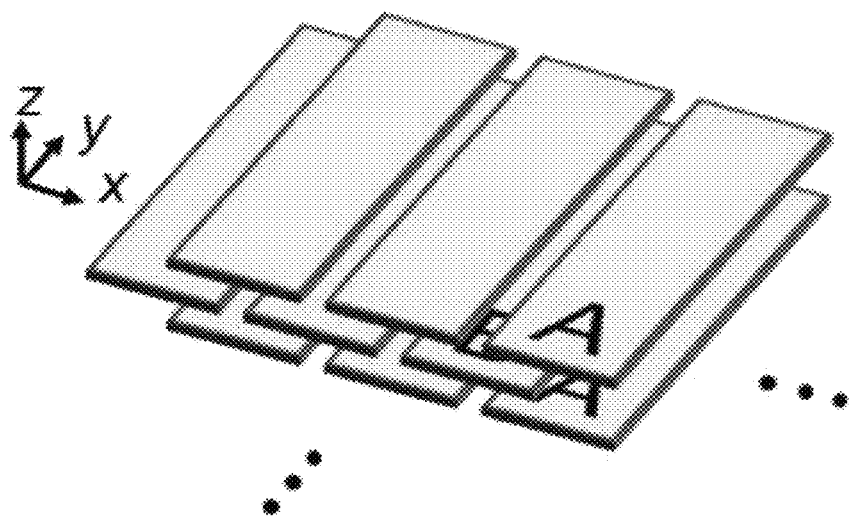
FIG. 13 shows the biaxial anisotropic mesoscopic crystal composed of metal ribbons (strips) which are shifted stacked.

FIG. 13 shows the biaxial anisotropic mesoscopic crystal composed of metal ribbons (strips) which are shifted stacked.

FIG. 13 shows the biaxial anisotropic mesoscopic crystal composed of metal ribbons (strips) which are shifted stacked. Also here, each metal ribbon is insulated by a filling dielectric. Here, $\varepsilon_x$ is extremely large due to the space-filling enhancement mechanism, $\varepsilon_y$ is similar order with $\varepsilon_m$, and $\varepsilon_z$ is similar order with $\varepsilon_d$.

Figure 14A:
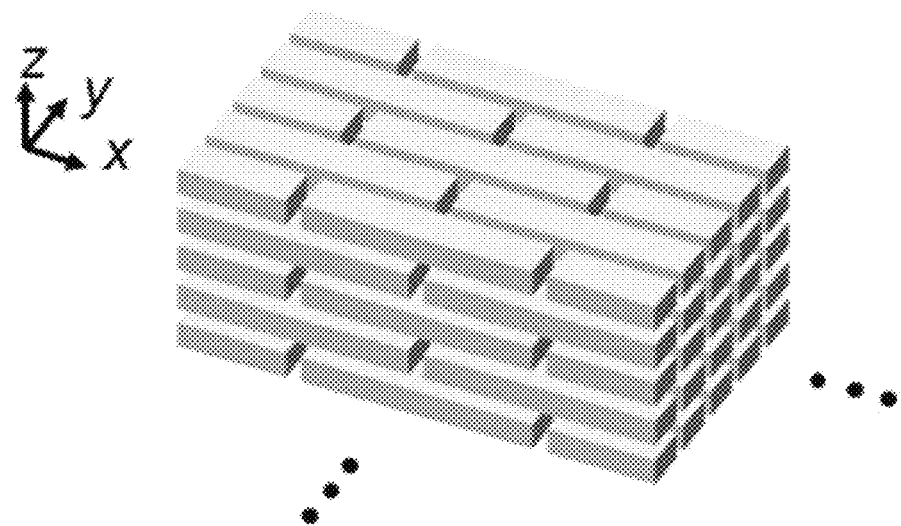
FIGS. 14A and 14B show the uniaxial anisotropic mesoscopic crystal composed of finite length of metal wires which are shifted stacked.
Figure 14B:
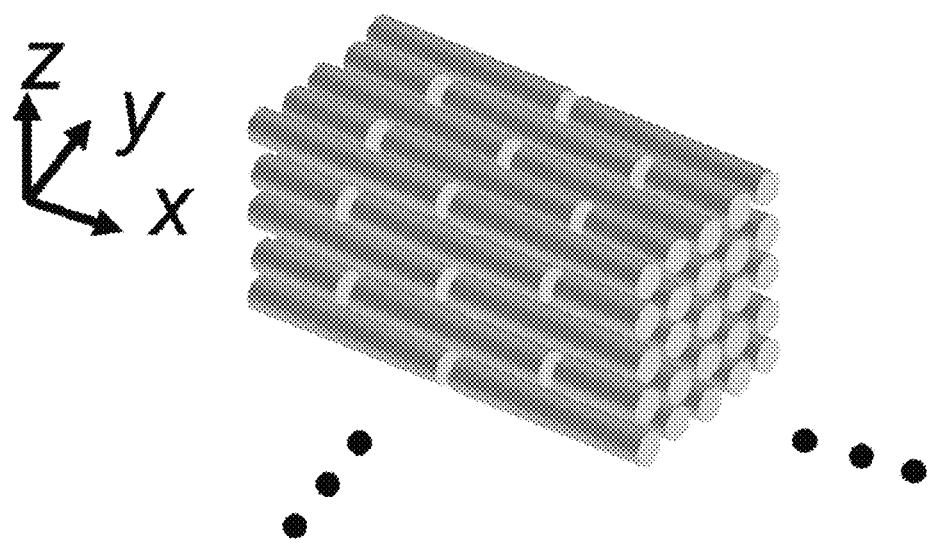

FIGS. 14A and 14B show the uniaxial anisotropic mesoscopic crystal composed of finite length of metal wires which are shifted stacked. FIG. 14A shows an example where the metal wires have a rectangular shape, but typically, metal wires have a cylindrical shape as shown in FIG. 14B. FIG. 14A is substantially identical to FIG. 14B in object and effect, and, thus, an explanation will be provided with reference to FIG. 14B.

FIG. 14B shows the uniaxial anisotropic mesoscopic crystal composed of finite length of metal wires which are shifted stacked. Also here, each metal wire is insulated by a filling dielectric. Here, $\varepsilon_x$ is extremely large due to the space-filling enhancement mechanism, and $\varepsilon_y$ and $\varepsilon_z$ are similar order with $\varepsilon_d$.

Figure 15A:
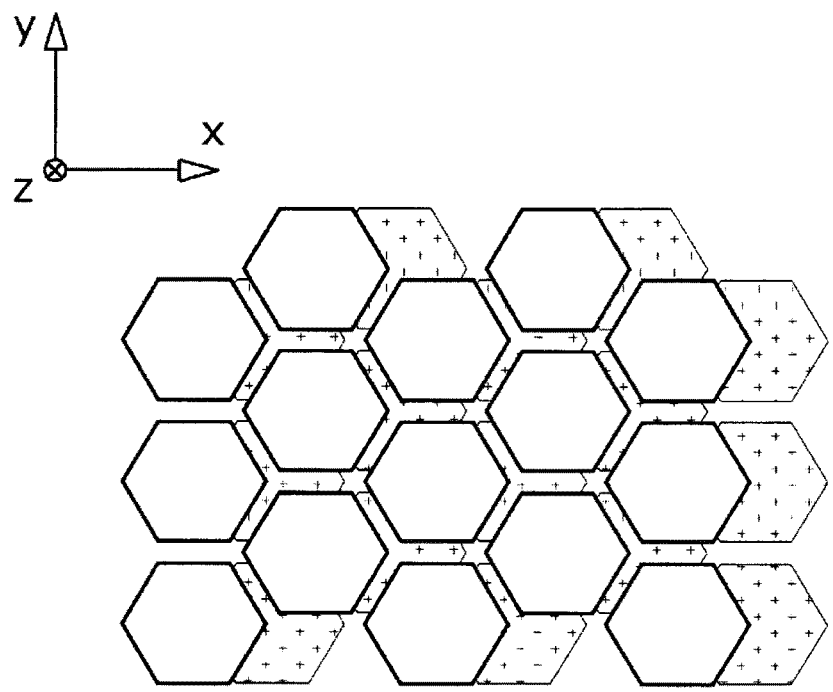
FIGS. 15A and 15B provide plane views of the uniaxial anisotropic mesoscopic crystal composed of hexagonal metallic plates which are shifted stacked.

FIG. 15A is a plane view of the uniaxial anisotropic mesoscopic crystal composed of hexagonal metallic plates which are shifted stacked.

FIG. 15A shows the uniaxial anisotropic mesoscopic crystal composed of hexagonal metallic plates which are shifted stacked. FIG. 15A shows the x-y plane view of the mesoscopic crystal. Also here, each metal plate is insulated by a filling dielectric. Here, similar with FIGS. 1A-1C, $\varepsilon_x$ and $\varepsilon_y$ are extremely large due to the space-filling enhancement mechanism, and $\varepsilon_z$ is similar order with $\varepsilon_d$.

Figure 15B:
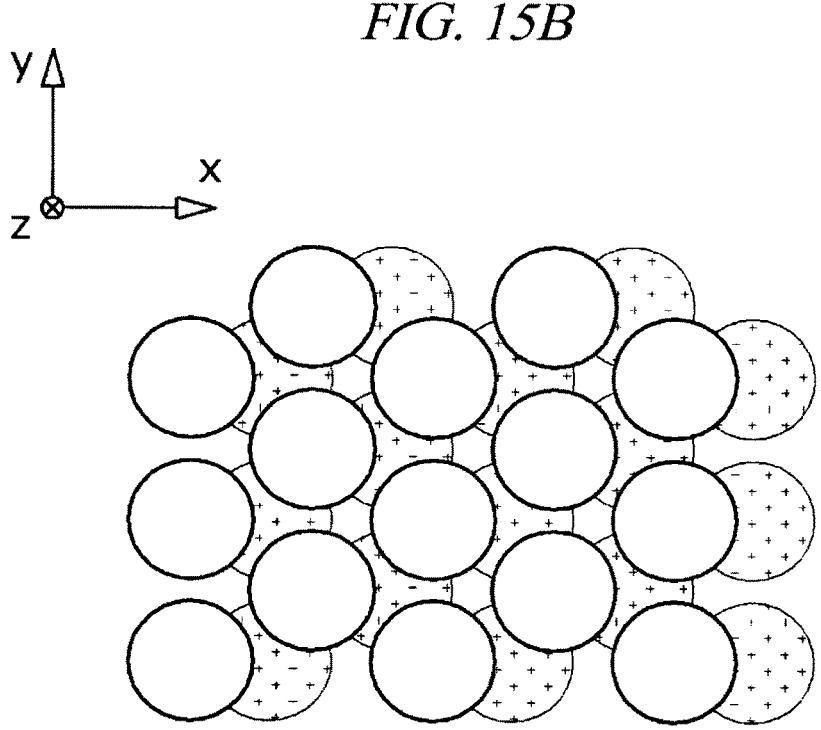

The hexagonal metallic plates in FIG. 15A may be substituted by circular metal plates, and FIG. 15B shows an example of a mesoscopic crystal structure including circular metal plates.

Figure 16:
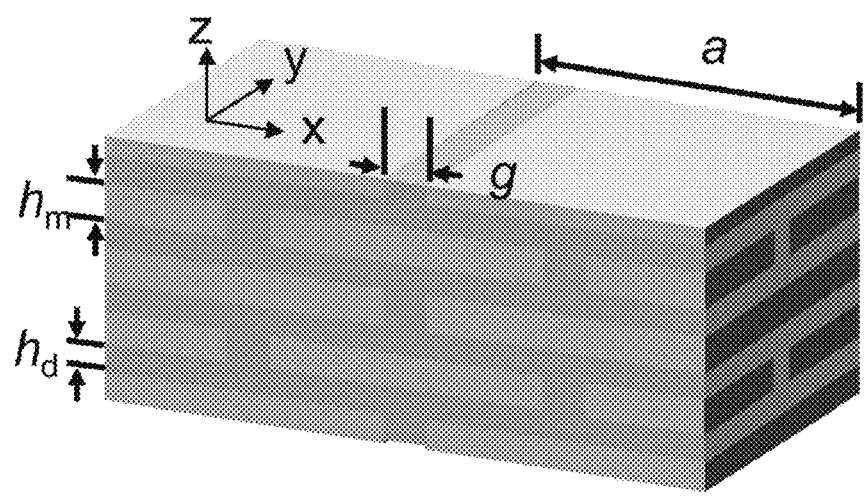
FIG. 16 is a schematic diagram provided to explain parameters of a mesoscopic crystal structure according to the present disclosure.

FIG. 16 is a schematic diagram provided to explain parameters of a mesoscopic crystal structure according to the present disclosure. Values of the given parameters a, g, $h_m$, and $h_d$ should be changed depending on a frequency.

Figure 17A:
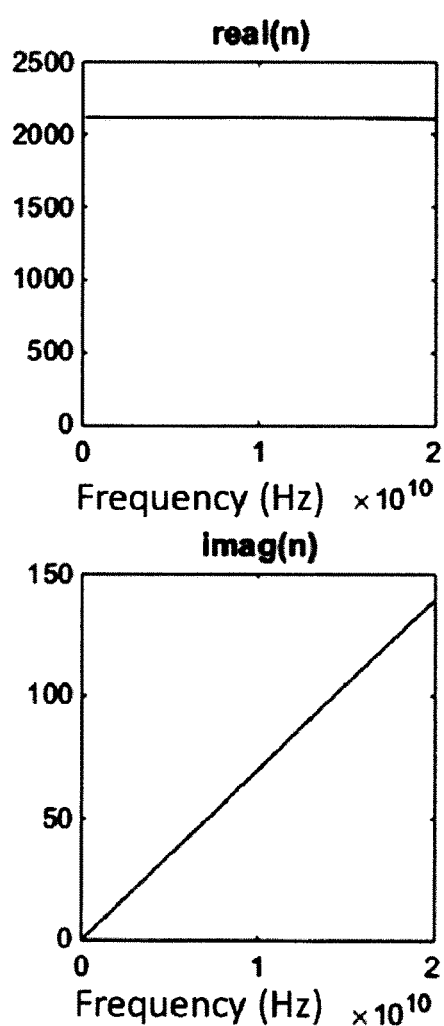
FIGS. 17A and 17B show graphs of refractive index and 3rd order susceptibility of a mesoscopic crystal structure according to the present disclosure depending on a frequency of around 10 GHz.
Figure 17B:
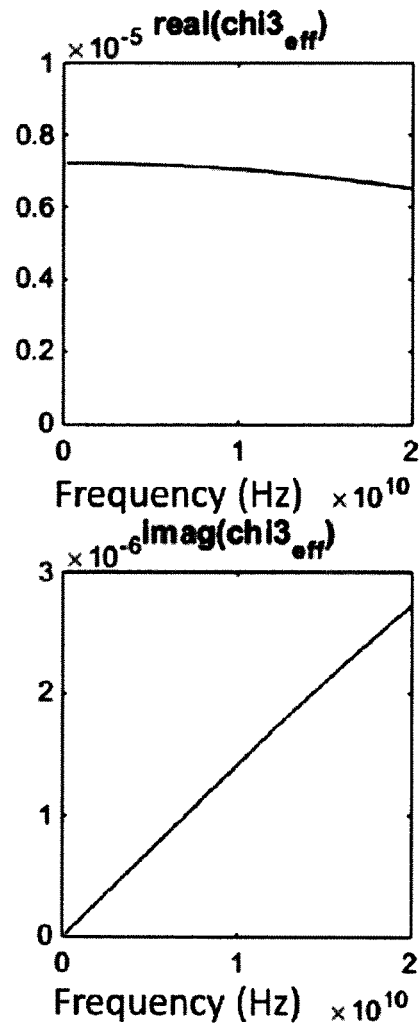

FIGS. 17A and 17B show graphs of refractive index and 3rd order susceptibility of a mesoscopic crystal structure according to the present disclosure depending on a frequency of around 10 GHz.

At a frequency around 10 GHz, a may be 1 mm or less, g may be 1/10 of a, $h_m$ may be 1 μm or less, and $h_d$ may be 1 μm or less as the parameters in FIG. 16, and the metal may be gold, copper, silver, and aluminum, and the dielectric may be any one of silica, silicon, polytetrafluoroethylenes, polydimethylsiloxanes, and acrylites.

FIGS. 17A and 17B show the refractive index and 3rd order susceptibility obtained assuming that copper is used as the metal, silica ($\varepsilon$=3.9) is used as the dielectric and the structural parameters include a=750 μm, g=120 μm, $h_m$=400 nm, and $h_d$=150 nm.

Figure 18A:
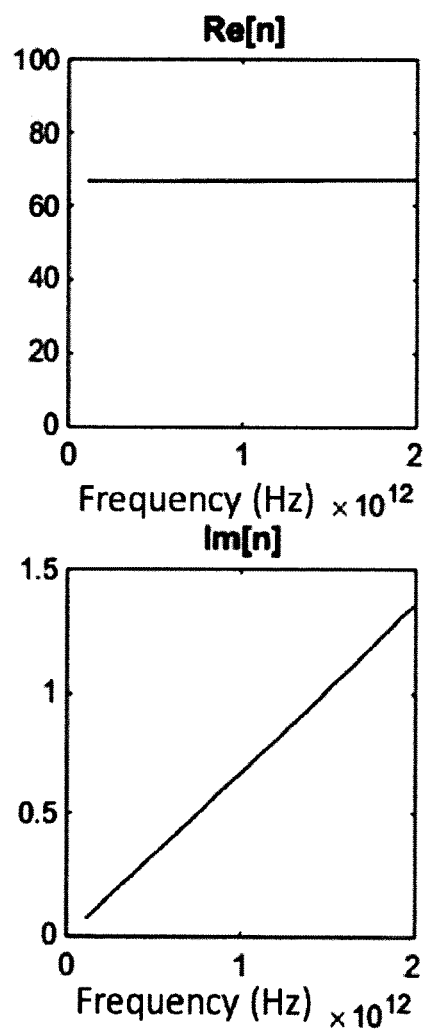
FIGS. 18A and 18B show graphs of refractive index and 3rd order susceptibility of a mesoscopic crystal structure according to the present disclosure depending on a frequency of around 1 THz.
Figure 18B:
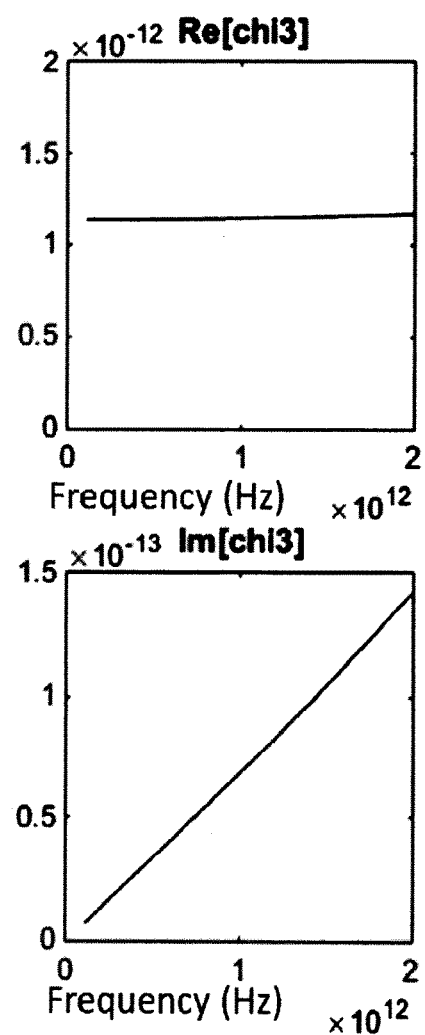

FIGS. 18A and 18B show graphs of refractive index and 3rd order susceptibility of a mesoscopic crystal structure according to the present disclosure depending on a frequency of around 1 THz.

At a frequency around 1 THz, a may be about several μm, g may be from 1/10 to 1/5 of a, $h_m$ may be about several ten nm, and $h_d$ may be about several ten nm as the parameters in FIG. 16, and the metal may be gold, silver, and aluminum, and the dielectric may be any one of silica, silicon, polytetrafluoroethylene, polydimethylsiloxane, and acrylite.

FIGS. 18A and 18B show the refractive index and 3rd order susceptibility obtained assuming that gold is used as the metal, zinc oxide ($\varepsilon$=8) is used as the dielectric and the structural parameters include a=1.8 μm, g=0.4 μm, $h_m$=20 nm, and $h_d$=20 nm.

Figure 19A:
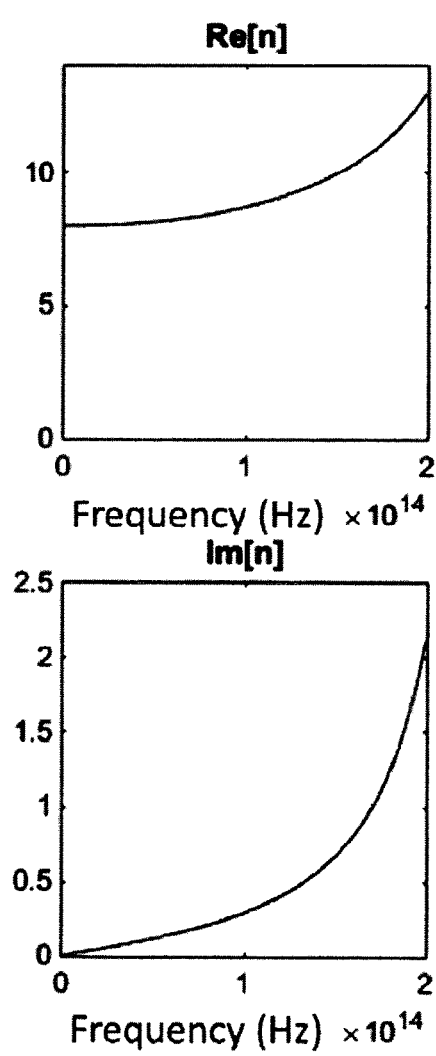
FIGS. 19A and 19B show graphs of refractive index and 3rd order susceptibility of a mesoscopic crystal structure according to the present disclosure depending on an infrared frequency.
Figure 19B:
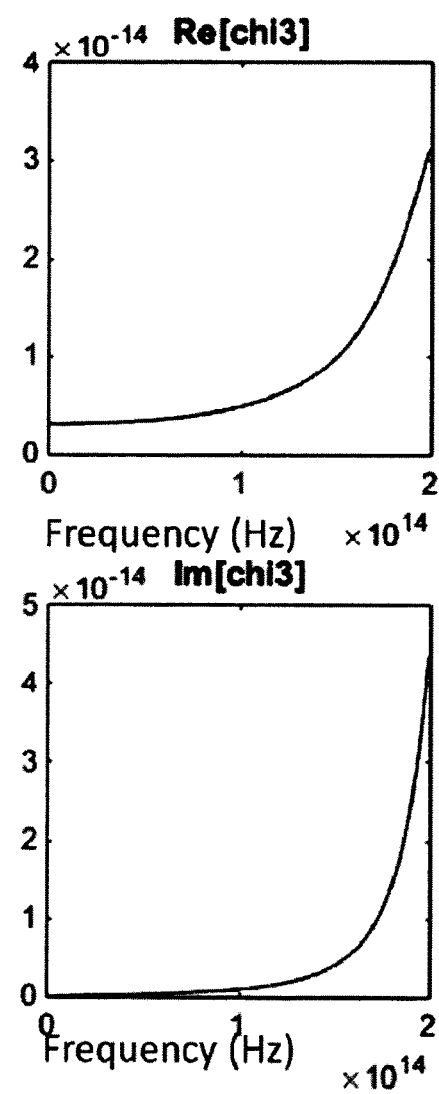

FIGS. 19A and 19B show graphs of refractive index and 3rd order susceptibility of a mesoscopic crystal structure according to the present disclosure depending on an infrared frequency.

At a frequency around infrared light, a may be about 100 nm, g may be from 1/10 to 1/5 of a, $h_m$ may be about several nm, and $h_d$ may be about several nm as the parameters in FIG. 16, and the metal may be silver and aluminum, and the dielectric may be any one of silica, silicon, polytetrafluoroethylenes, polydimethylsiloxanes, and acrylites.

FIGS. 19A and 19B show the refractive index and 3rd order susceptibility obtained assuming that gold is used as the metal, silica ($\varepsilon$=2) is used as the dielectric and the structural parameters include a=75 nm, g=5 nm, $h_m$=5 nm, and $h_d$=5 nm.

Figure 20:
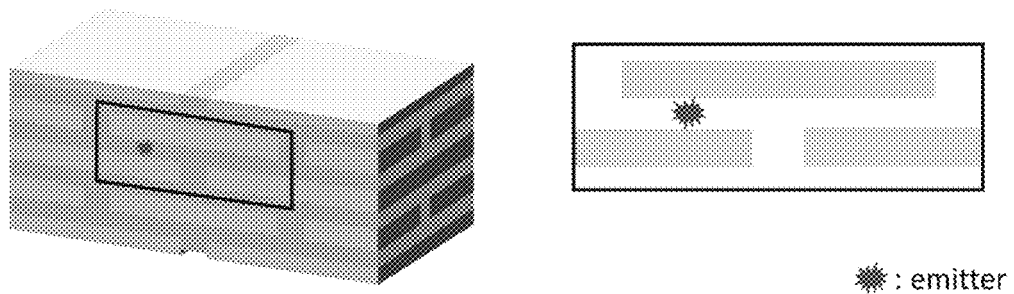
FIG. 20 is a conceptual diagram provided to explain a high-speed emitter with a low loss in the case where the emitter is included in a mesoscopic crystal structure according to the present disclosure.

FIG. 20 is a conceptual diagram provided to explain a high-speed emitter with a low loss in the case where the emitter is included in a mesoscopic crystal structure according to the present disclosure.

In the case where an illuminant such as a dye molecule is present within a structure, a spontaneous emission rate is increased by a Purcell factor. If the illuminant is appropriately positioned in the structure of the present disclosure, the spontaneous emission rate is increased as the refractive index is increased by a refractive index enhancement effect. An increase in Purcell factor using a conventional metal structure includes an actually relatively small increase in radiative emission rate due to inherent light absorption by metal, but in the present structure, a high refractive index can be obtained in a quasi-static region with less light absorption by metal, and, thus, a radiative emission rate can be greatly increased.

Figure 21:
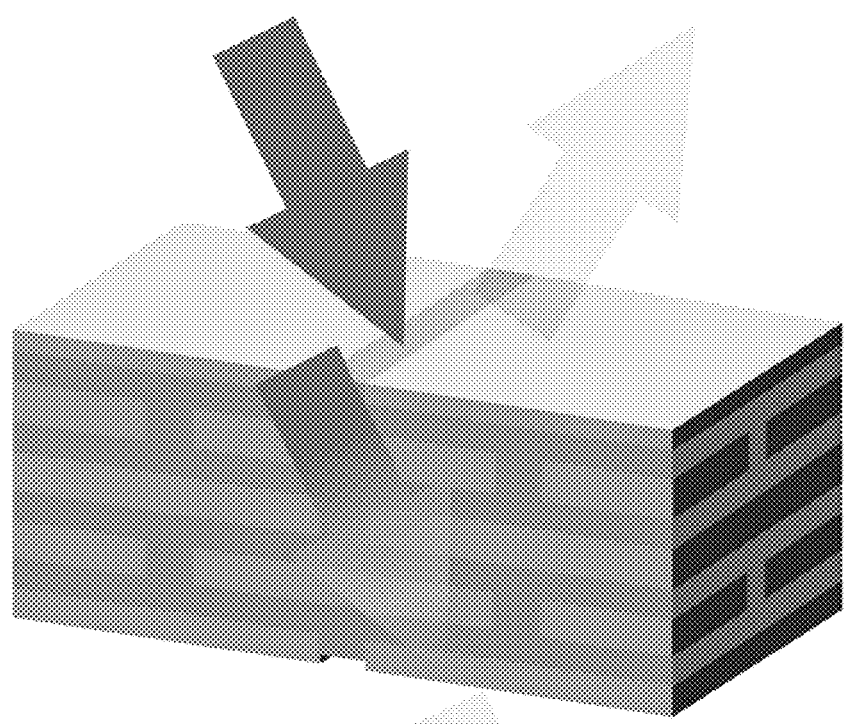
FIG. 21 is a conceptual diagram provided to explain a light absorber using a mesoscopic crystal structure according to the present disclosure.

FIG. 21 is a conceptual diagram provided to explain a light absorber using a mesoscopic crystal structure according to the present disclosure.

The maximum absorption rate of an optical material, such as silicon, organic semiconductor, and dye, having a suitable absorption rate is proportional to the Yablonovitch limit, i.e., the square of the refractive index. The structure according to the present disclosure is configured to greatly increase the refractive index and thus can greatly increase the absorption rate. Herein, a high refractive index can be obtained in a quasi-static region with less absorption by metal, and, thus, it is possible to greatly increase the light absorption rate of a filling dielectric which can be actually used rather than the loss of metal. Herein, as the filing dielectric, silicon (amorphous or the like), inorganic semiconductor materials such as GaAs, Ge, or the like, organic semiconductor materials, a dye, or the like may be used depending on application.

Figure 22:
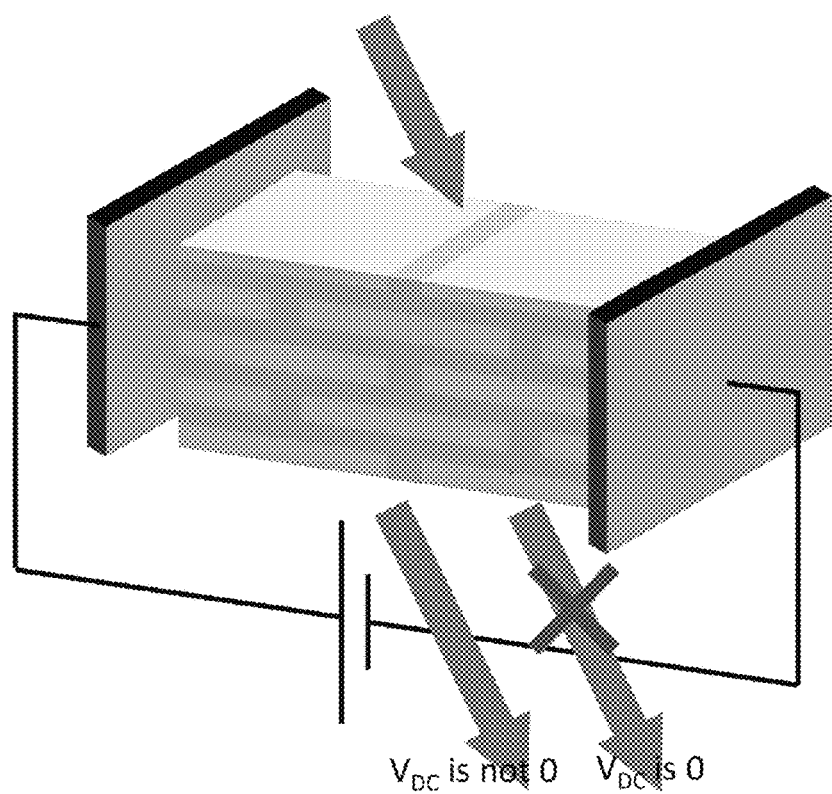
FIG. 22 is a diagram provided to explain a method of using a mesoscopic crystal structure according to the present disclosure in a dielectric whose effective dielectric constant varies depending on an external electric field.

FIG. 22 is a diagram provided to explain a method of using a mesoscopic crystal structure according to the present disclosure in a dielectric whose effective dielectric constant varies depending on an external electric field.

Conventionally, a material whose optical properties are changed upon application of a DC electric field has also been used, but the use of the mesoscopic crystal structure according to the present disclosure can make it possible to increase an optical phase difference depending on the presence or absence of a DC (or low frequency) electric field even in a very thin structure and also possible to obtain a sensitive resonance and thus possible to implement a very small electro-optic modulator.

Figure 23:
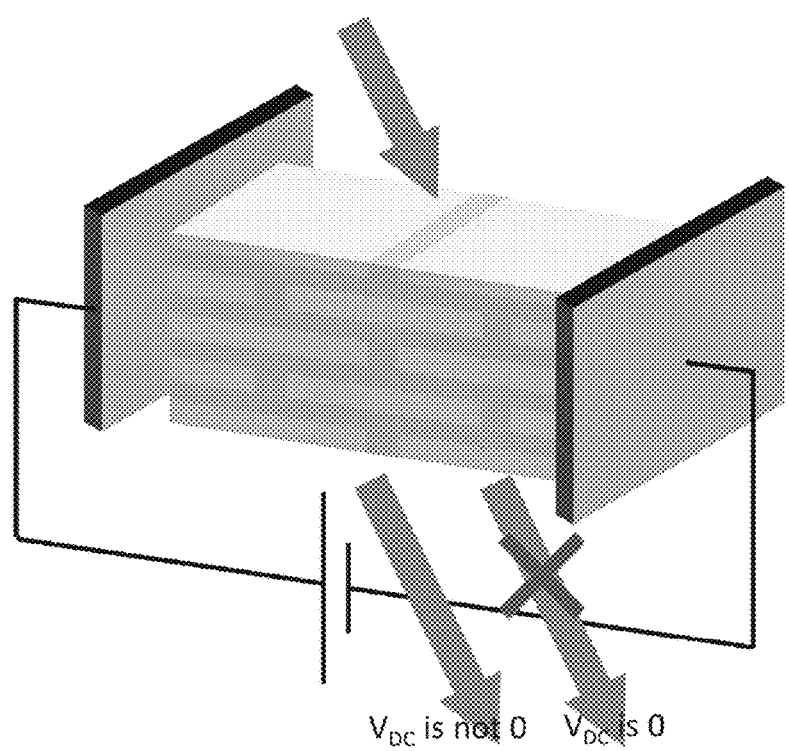
FIG. 23 is a conceptual diagram provided to explain a method of precisely measuring a dielectric constant of a dielectric fluid using a mesoscopic crystal structure according to the present disclosure.

FIG. 23 is a conceptual diagram provided to explain a method of precisely measuring a dielectric constant of a dielectric fluid using a mesoscopic crystal structure according to the present disclosure.

The mesoscopic crystal structure according to the present disclosure greatly increases the dielectric constant and refractive index of a filling dielectric. If a fluid system is fabricated using this mesoscopic crystal structure as shown in FIG. 23, the refractive index of the mesoscopic crystal structure is greatly changed by a slight change in refractive index of an internal dielectric fluid. If the refractive index of the mesoscopic crystal structure is found by an optical method or the like, the refractive index of the internal dielectric fluid can be measured very accurately or a slight change in refractive index can be detected.

Figure 24:
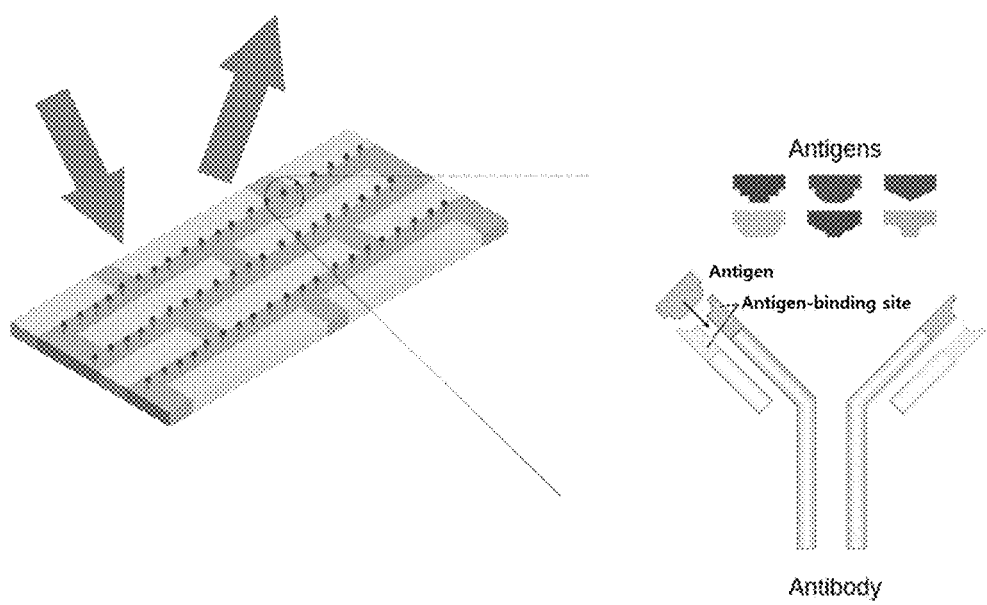
FIG. 24 is a conceptual diagram provided to explain a method of measuring a density of an antigen using a mesoscopic crystal structure according to the present disclosure.

FIG. 24 is a conceptual diagram provided to explain a method of measuring a density of an antigen using a mesoscopic crystal structure according to the present disclosure.

If an antibody is attached to a dielectric portion in a structure as shown in FIG. 24, the dielectric is slightly changed in effective refractive index between when an antigen is attached thereto and when the antigen is detached therefrom. The structure according to the present disclosure can greatly increase the refractive index of a filling dielectric, and, thus, a slight change in refractive index of the filling dielectric can be detected, and therefore, if a sensor as described above is fabricated, the concentration of an antigen can be measured by an optical method or an electric method with high susceptibility.

Figure 25:
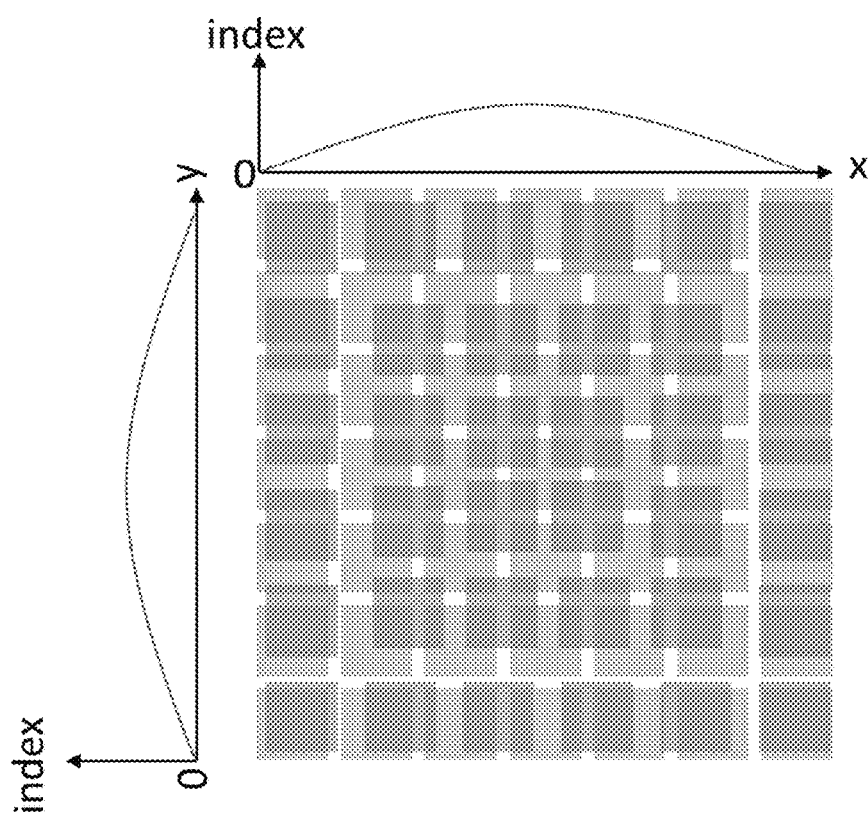
FIG. 25 is a diagram provided to explain a method of fabricating a plane lens using a modification of a mesoscopic crystal structure according to the present disclosure.

FIG. 25 is a diagram provided to explain a method of fabricating a plane lens using a modification of a mesoscopic crystal structure according to the present disclosure.

As shown in FIG. 25, metal plates in some metal layers (green) may be spatially arranged on different cycles and thus may be different in an area overlapped with other metal layers (yellow). In the mesoscopic crystal structure of the present disclosure, the overlapped area is approximately proportional to the refractive index, and, thus, in the above-described structure, the refractive index varies depending on the space. The above-described example shows the structure having a high refractive index at the center and a low refractive index on the periphery, which can be used as a lens.

Figure 26:
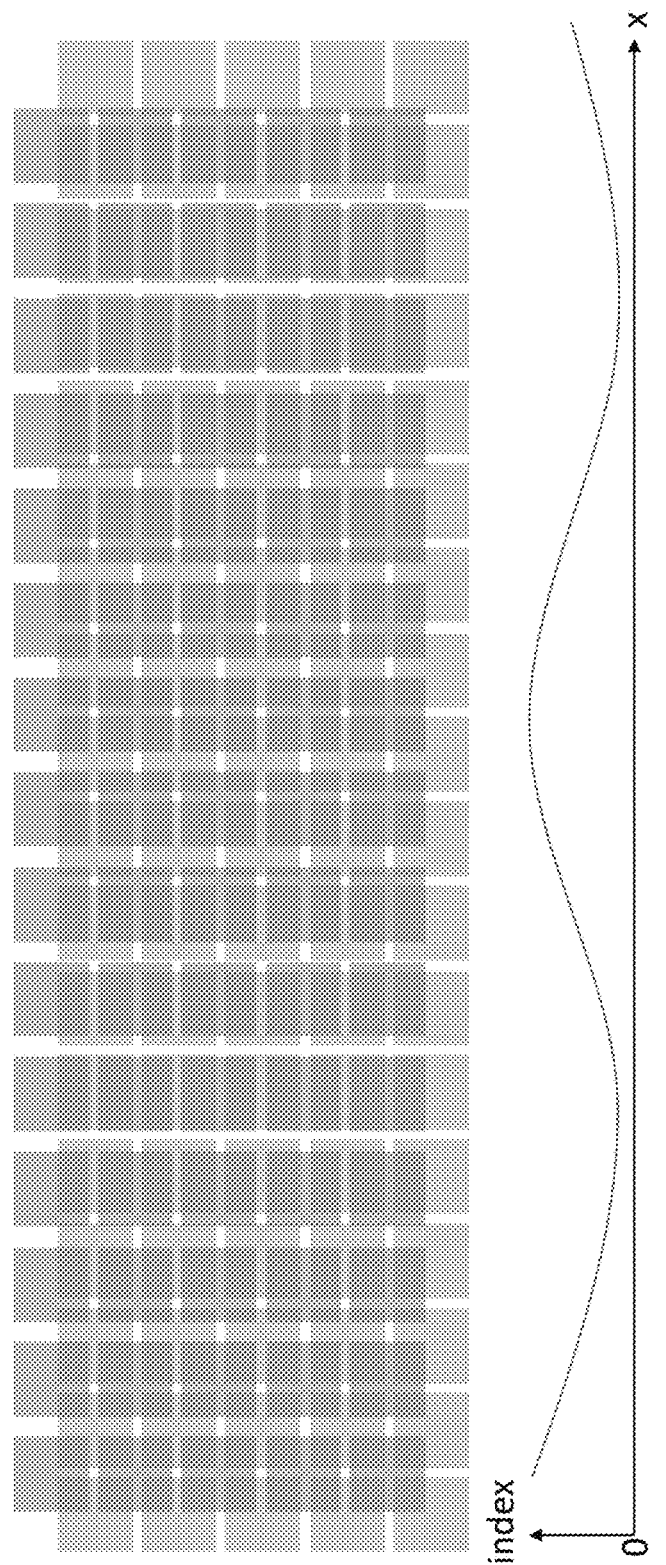
FIG. 26 is a diagram provided to explain a refractive index-grating device using a mesoscopic crystal structure according to the present disclosure.

FIG. 26 is a diagram provided to explain a refractive index-grating device using a mesoscopic crystal structure according to the present disclosure.

As shown in FIG. 26, metal plates in any metal layer may overlap metal plates in another metal layer on different cycles and thus may be different in an overlapped area on a cycle like a Moire interference pattern. In this case, the refractive index also varies depending on the space on a cycle, and this structure can be used as a grating structure with index contrast.

The mesoscopic crystal structure according to the present disclosure has a high optical nonlinearity and thus can be used for an optical device requiring nonlinearity.

The optical nonlinearity widely applies to engineering and real world, such as optical up-conversion, optical switching, and optical memories. However, the optical nonlinearity is generally very small compared to other physical phenomena, such as chemical reactions and electric signals in circuitry. Therefore, most of optical nonlinear phenomena are only realized by intense laser light. For this reason, there have been numerous efforts to enhance the optical nonlinearity of the light medium.

There are classical and quantum mechanical approaches to enhance the optical nonlinearity via resonance engineering. Most classical approaches exploit micro- or nano-sized metallic resonators. The strong electromagnetic field can be obtained at the targeted resonance frequency, and the effective nonlinearity enhances at these frequencies. Quantum mechanically, energy levels are designed and manipulated to enhance nonlinearity at specific frequencies. However, both resonance-based enhancement approaches efficiently enhance the optical nonlinearity only near the specific frequency range. Moreover, if an enhancement factor is designed to have a larger value, the enhancement frequency bandwidth becomes narrower. The enhancement and frequency have trade-off relationship. Also, the resonance frequency is dependent on the fabrication margin.

The non-resonance-based nonlinearity enhancement has also been proposed. However, the degree of enhancement is moderate to compare the resonance-based approaches.

Herein, there is provided a general route to enhance the magnitude of the nonlinear susceptibility within quasi-static regime with the degree of enhancement larger than conventional resonance-based approaches. Using this scheme, we show that the $x^{(3)}$ enhancement factor of $10^5$ for terahertz, and $10^3$ for near IR with numerical simulation. Moreover, not only the magnitude of nonlinear susceptibility can be enhanced but also the tensor components can be intendedly manipulated. This gives additional degree of freedom of engineering nonlinear susceptibility and can be critical to real applications.

Analytical Model (FIGS. 1A-1C)

The nonlinear constitutive relation, specifically 3rd order nonlinear polarization, of the natural crystal can be determined by $P^{(3)} = \tilde{X}^{(3)} E^{(3)}$.

(where, $P^{(3)} = [P_x^{(3)}, P_y^{(3)}, P_z^{(3)}]^t$
$E^{(3)} = [E_x^3, E_y^3, E_z^3, 3E_x^2 E_y, 3E_y^2 E_z, 3E_y^2 E_x, 3E_z^3 E_x, 3E_z^2 E_y, 6E_x E_y E_z]^t$)

$\tilde{X}^{(3)}$ represents a 3-by-10 nonlinear susceptibility tensor. Similarly, the homogenized constitutive relation of mesoscopic crystal can be represented as $P_{eff}^{(3)} = \tilde{M}_1 \tilde{X}^{(3)} \tilde{M}_2^{(3)} E_{eff}^{(3)}$. Herein, $\tilde{M}_1$ and $\tilde{M}_2^{(3)}$ are tensors that enhance and manipulate the tensor component of nonlinear dielectric matrix $\tilde{x}^{(3)}$.

Before establishing explicit expression for tensor components of $\tilde{X}_{eff}^{(3)} (=\tilde{M}_1 \tilde{x}^{(3)} \tilde{M}_2^{(3)})$, it is convenient to consider unitless equi-potential surface $(aV_{eff,q}, 0 \leq a \leq 1)$ arising from q-directional effective potential, $V_{eff,q}(q=x,y,z)$. A equi-potential surface vector field $S_{q,a}(x,y,z)$ is defined on the surface $((x_s, y_s, z_s))$ with the magnitude and direction of $$-\frac{\nabla V_q(x,y,z)}{|\nabla V_q(x,y,z)|}.$$

Here, $V_q$ is local voltage distribution due to the q-directional effective potential, $V_{eff,q}$. The integrating tensor $\tilde{M}_1$ relates local polarization $P_{loc}(x,y,z)$ to averaged polarization $(P_{eff})$. That is, $P_{eff} = \tilde{M}_1 P_{loc}(x,y,z)$. The explicit form of the $\tilde{M}_1$ can be found by divergence free nature of polarization. Since $\oint_a P_{loc} \cdot \hat{n} da = 0$, total electric flux across the any surface which has a common boundary is equivalent. To calculate q-directional component of averaged polarization $(P_{eff,q})$, $S_{q,a}(x,y,z)$ with any a can be chosen for simpler calculation since the boundary of $S_{q,a}(x,y,z)$ is q-normal cross section of a unit cell due to the symmetry. That is, $$P_{eff,q} = \frac{l_q}{l_x l_y l_z} \int P_{loc} \cdot S_{q,a} da,$$

and an effective polarization vector $(P_{eff})$ can be represented as shown in Equation 11.

$$P_{eff} = \tilde{M}_1 P_{loc}(x,y,z), \text{ where} \quad [\text{Equation 11}]$$

$$\tilde{M}_1 = \begin{bmatrix} \frac{1}{l_y l_z}\int \hat{x}\cdot S_{x,a}da & \frac{1}{l_y l_z}\int \hat{y}\cdot S_{x,a}da & \frac{1}{l_y l_z}\int \hat{z}\cdot S_{x,a}da \\ \frac{1}{l_z l_x}\int \hat{x}\cdot S_{y,a}da & \frac{1}{l_z l_x}\int \hat{y}\cdot S_{y,a}da & \frac{1}{l_z l_x}\int \hat{z}\cdot S_{y,a}da \\ \frac{1}{l_x l_y}\int \hat{x}\cdot S_{z,a}da & \frac{1}{l_x l_y}\int \hat{y}\cdot S_{z,a}da & \frac{1}{l_x l_y}\int \hat{z}\cdot S_{z,a}da \end{bmatrix}$$

or simply, $$M_{1,ij} = \frac{l_i}{l_x l_y l_z}\int \hat{j}\cdot S_{i,a}(x,y,z)da$$

The integrating matrix $M_1$ can be applied to the calculation of both linear and nonlinear polarizations.

The localizing tensor $\tilde{M}_2^{(3)}(x,y,z)$ relates averaged (effective) electric field to local electric field, i.e., $$E_{loc}^3(x,y,z) = \tilde{M}_2^{(3)}(x,y,z) E_{eff}.$$

The explicit form of tensor components of $\tilde{M}_2^3$ can be found by considering linear relationship between a local field and an effective field, $E_{loc}(x,y,z) = \tilde{M}_2^{(1)}(x,y,z) E_{eff}$. For a quasi-static case, a local electric field can be derived from the spatial derivative of local electric potential, and, thus, the local electric field for the (x,y,z) point can be represented as $E_{loc} = -\nabla V_q(x,y,z) = m_q(x,y,z) S_q(x,y,z) E_{eff,q}$, where a unitless magnification factor $$m_q = \left|-\frac{1}{E_{eff,q}}\nabla V_q(x,y,z)\right|,$$

and a unitless vector field $$S_q(x,y,z) = -\frac{\nabla V_q(x,y,z)}{|\nabla V_q(x,y,z)|}.$$

Thus, $S_q(x,y,z)$ is a superset of $S_{q,a}(x,y,z)$, i.e., $S_q(x,y,z) = \{S_{q,a}(x,y,z) | 0 \leq a \leq 1\}$. The electric potential only changes within a dielectric matrix for the perfect conducting metallic inclusions, so the $S_q(x,y,z)$ is 1 for dielectric region and not defined inside the perfect conducting metal. The local electric field vector can be represented as shown in Equation 12.

$$E_{loc}(x,y,z) = \tilde{M}_2^{(1)}(x,y,z) E_{eff}, \quad [\text{Equation 12}]$$

$$\text{where } \tilde{M}_2^{(1)}(x,y,z) = \begin{bmatrix} m_x S_x\cdot\hat{x} & m_y S_y\cdot\hat{x} & m_z S_z\cdot\hat{x} \\ m_x S_x\cdot\hat{y} & m_y S_y\cdot\hat{y} & m_z S_z\cdot\hat{y} \\ m_x S_x\cdot\hat{z} & m_y S_y\cdot\hat{z} & m_z S_z\cdot\hat{z} \end{bmatrix}$$

or more simply, $\tilde{M}_{2,ij}^{(1)}(x,y,z) = m_j(x,y,z) S_j(x,y,z)\cdot\hat{i}$ The explicit form of $\tilde{M}_2^{(3)}(x,y,z)$ for the nonlinear constitutive relation can be found from Equation 5, and $P_{loc}^{(3)}(x,y,z) = \tilde{X}^{(3)} \tilde{M}_2^{(3)} E_{eff}^3$.

To summarize, the explicit form of nonlinear constitutive relation of the mesoscopic crystal can be written as $P_{eff}^{(3)} = \tilde{X}_{eff}^{(3)} E_{eff}^3$ with an effective $3^{rd}$ order nonlinear susceptibility tensor, $\tilde{X}_{eff}^{(3)} = \tilde{M}_1 \tilde{X}^{(3)} \tilde{M}_2^{(3)}$. Manipulation tensors $\tilde{M}_1$ and $\tilde{M}_2^{(3)}$ can also be obtained.

To obtain components of the effective $3^{rd}$ order nonlinear susceptibility tensor $\tilde{X}_{eff}^{(3)}$ for the mesoscopic crystal structure of the present disclosure, $\tilde{X}_{eff}^{(3)}$ is calculated for reduced 2-dimensional matrix structures and an equi-potential surface becomes contour. First, $\tilde{X}_{eff\ 11}^{(3)} (=\tilde{X}_{eff\ xxxx}^{(3)}) = \Sigma_i M_{1,1i} \tilde{X}^{(3)} M_{2,i1}^{(3)}$. To calculate $M_{1,1i}$, $a = \frac{3}{4}$ can be chosen to obtain $S_{x,3/4}$. Since $S_x\cdot\hat{y} = 0$ and $(S_x\cdot\hat{x})(S_x\cdot\hat{z}) = 0$, if we neglect a fringe field, most terms vanish for $M_{1,1i}$ and $M_{2,i1}^{(3)}$, and the above equation is reduced to Equation 13.

$$X_{eff\ 11}^{(3)} = \left[\frac{1}{l_z}\int \hat{x}\cdot S_{x,\frac{3}{4}}da, 0, \frac{1}{l_z}\int \hat{z}\cdot S_{x,\frac{3}{4}}da\right] \tilde{X}^{(3)} m_x^3 \quad [\text{Equation 13}]$$

$$[(S_x\cdot\hat{x})^3, 0, (S_x\cdot\hat{z})^3, 0, 0, 0, 0, 0, 0, 0]^t =$$

$$m_x^3 \left(X_{11}^{(3)}\frac{1}{l_z}\int (\hat{x}\cdot S_{x,3/4})^4 da + X_{33}^{(3)}\frac{1}{l_z}\int (\hat{z}\cdot S_{x,3/4})^4 da\right)$$

-continued

That is, $\chi_{\text{eff}11}^{(3)} = \left(\frac{a}{2g}\right)^3 \chi_{11}^{(3)}\left(\frac{2g}{4g}\right) + \left(\frac{a}{2g}\right)^3 \chi_{33}^{(3)}\left(\frac{a-2g}{4g}\right)$ $\chi_{\text{eff}11}^{(3)} = \left(\frac{a}{2g}\right)^3 \chi_{11}^{(3)}\left(\frac{2g}{4g}\right) + \left(\frac{a}{2g}\right)^3 \chi_{33}^{(3)}\left(\frac{a-2g}{4g}\right)$ Similarly, $\therefore$ $\chi_{\text{eff}11}^{(3)} \approx \frac{1}{16}\left(\frac{a}{g}\right)^3 \chi_{11}^{(3)} + \frac{1}{32}\left(\frac{a}{g}\right)^4 \chi_{33}^{(3)}$ (for $a \gg g$)

By these procedures, all components of effective nonlinear susceptibility tensor of the mesoscopic crystal structure according to the present disclosure can be obtained, and the $3^{rd}$ order nonlinear susceptibility tensor can be represented as shown in Equation 14.

The nonlinear susceptibility of the mesoscopic crystal structure in terahertz frequencies can be obtained with finite difference time domain (FDTD) simulation. Herein, gold is used as a metal and zinc oxide is used as a nonlinear dielectric layer. The structural parameters may include a=10 μm, g=100 nm (aspect ratio a/g=100), and the mesoscopic crystal slab is treated as an effective slab. The transfer matrix method with the obtained reflection and transmission coefficients for fundamental frequencies is used to obtain linear optical property. To obtain nonlinear electric susceptibility, the nonlinear transfer matrix method is utilized with a numerically obtained amplitude of backward and forward $3^{rd}$ harmonic wave. The FOM is obtained using the obtained refractive index. The refractive index is around 200 for frequency range from 0.1 THz to 2 THz, and the FOM is 10 or more.

$$\tilde{\chi}_{\text{eff}}^{(3)} = [p\,q\,r]^t$$ [Equation 14]

$$p = \begin{bmatrix} \frac{1}{16}\left(\frac{a}{g}\right)^3 \chi_{11} + \frac{1}{32}\left(\frac{a}{g}\right)^4\left(1-\frac{2g}{a}\right)^2 \chi_{33} \\ 0 \\ 0 \\ 0 \\ 0 \\ 0 \\ \frac{1}{32}\left(\frac{a}{g}\right)^4\left(1-\frac{2g}{a}\right)^2 \chi_{33} \\ \frac{1}{2}\left(\frac{a}{g}\right)^2\left(1-\frac{2g}{a}\right)^2 \chi_{33} \\ 0 \\ 0 \end{bmatrix},$$

$$q = \begin{bmatrix} 0 \\ \frac{1}{16}\left(\frac{a}{g}\right)^3 \chi_{22} + \frac{1}{32}\left(\frac{a}{g}\right)^4\left(1-\frac{2g}{a}\right)^2 \chi_{33} \\ 0 \\ \frac{1}{32}\left(\frac{a}{g}\right)^4\left(1-\frac{2g}{a}\right)^2 \chi_{33} \\ 0 \\ 0 \\ 0 \\ 0 \\ \frac{1}{2}\left(\frac{a}{g}\right)^2\left(1-\frac{2g}{a}\right)^2 \chi_{33} \\ 0 \end{bmatrix}, \quad r = \begin{bmatrix} 0 \\ 0 \\ 8\left(1-\frac{2g}{a}\right)^2 \chi_{33} \\ 0 \\ \frac{1}{2}\left(\frac{a}{g}\right)^2\left(1-\frac{2g}{a}\right)^2 \chi_{33} \\ \frac{1}{2}\left(\frac{a}{g}\right)^2\left(1-\frac{2g}{a}\right)^2 \chi_{33} \\ 0 \\ 0 \\ 0 \\ 0 \end{bmatrix}$$

For example,

For $\frac{a}{g} = 100$, $\tilde{\chi}^{(3)}$ becomes $\tilde{\chi}_{\text{eff}}^{(3)} =$ $$\begin{bmatrix} 62500\,\chi_{11} + 3\times10^6 \chi_{33} & 0 & 0 & 0 & 0 & 0 & 3\times10^6 \chi_{33} & 4800\,\chi_{33} & 0 & 0 \\ 0 & 62500\,\chi_{22} + 3\times10^6 \chi_{33} & 0 & 3\times10^6 \chi_{33} & 0 & 0 & 0 & 0 & 4800\,\chi_{33} & 0 \\ 0 & 0 & 8\chi_{33} & 0 & 4800\,\chi_{33} & 4800\,\chi_{33} & 0 & 0 & 0 & 0 \end{bmatrix}$$

The magnitude of the effective nonlinear electric susceptibilities of the mesoscopic crystal can be classified into two cases: (1) $X_{ij}^{(3)}=0$ except for $X_{33}^{(3)}=1\times10^{-18}$; and (2) $X_{ij}^{(3)}=0$ except for $X_{11}^{(3)}=1\times10^{-18}$. The numerically obtained and analytically calculated values well agree, and as expected in the analytic model, the effective nonlinear susceptibility much enhances $X_{33}^{(3)}$. The nonlinearity enhancement of the mesoscopic crystal according to the present disclosure has a uniform enhancement factor over broad frequency range which is unusual for conventional resonant-based nonlinearity enhancement methods. The conventional resonant-based nonlinearity enhancement methods achieve the enhancement factor of $10^4$, whereas the nonlinearity enhancement of the mesoscopic crystal according to the present disclosure achieves the enhancement factor of $10^6$.

The extreme enhancement of $10^6$ is based on the space-filling nature of the nonlinear polarization.

When $X_{33}^{(3)}=1\times10^{-18}$ for a frequency of 1 THz, the enhancement factor shows the $4^{th}$ power of the aspect ratio, and when $X_{11}^{(3)}=1\times10^{-18}$, the enhancement factor shows the $3^{rd}$ power of the aspect ratio. However, in both cases, the $3^{rd}$ power of the enhancement factor is originated from the increase in local electric field magnitude compared with the effective electric field (averaged electric field) magnitude. This can be predicted from $E_{loc}(x,y,z)=\tilde{M}_2^{(3)}(x,y,z)E_{eff}^3$. The local electric field magnitude become $$\frac{a}{2g}$$

times larger than the effective electric field when the effective electric field is applied in the x-direction. Since the magnitude of $3^{rd}$ order nonlinear polarization is proportional to the $3^{rd}$ power of the effective electric field magnitude, a local nonlinear dipole moment is proportional to $$\left(\frac{a}{2g}\right)^3.$$

The previous work for enhancing linear optical property with quasi-static boundary condition may have the potential enhancement of $3^{rd}$ order nonlinear susceptibility, but a slight deviation from the exact cubic dependence is originated from the finite conductivity of the metal.

However, the most noticeable aspect of the nonlinear mesoscopic crystal according to the present disclosure is the additional enhancement factor of $$\frac{a}{g}.$$

This factor is originated from the denser local polarization for higher aspect ratio. That is, $P_{eff}=\tilde{M}_1 P_{loc}(x,y,z)$. In averaging the local nonlinear polarization, equi-potential contour (surface), $S_{x,a}$ is chosen, and this line forms a space-filling curve. Therefore, as the aspect ratio increases, the length of $S_{x,a}$ corresponding to a fixed length in the z-direction also increases. Thus, as the aspect ratio increases, the local nonlinear polarization is more densely integrated into the averaged nonlinear polarization. Among the entire length of $S_{x,a}$, only the partial length corresponding to the z-directional local nonlinear polarization increases as the aspect ratio increases. This is the reason for the $4^{th}$ power of the aspect ratio enhancement only occurs for $X_{33}^{(3)}$. Qualitatively, it can be understood as the major volume of the nonlinear dielectric possess the z-directional local nonlinear polarization. Since the aspect ratio can be order of 2 (several hundred times) for terahertz frequencies, the enhancement of nonlinear susceptibility of the mesoscopic crystal of the present disclosure is several order higher than the previous work. This enhancement originated from space-filling of a local dipole moment not only applies to $3^{rd}$ order nonlinear dipoles, but also applies to linear dipoles and nonlinear dipoles of various order. The investigated effective nonlinear susceptibility component is $X_{eff\,11}^{(3)}=X_{eff\,xxxx}^{(3)}$ and it almost entirely depends on $X_{33}^3$. The carefully designed manipulation tensors $\tilde{M}_1$ and $\tilde{M}_2^{(3)}(x,y,z)$ influence the effective nonlinear susceptibility tensor by $\tilde{X}_{eff}^{(3)}=\tilde{M}_1 \tilde{X}^{(3)} \tilde{M}_2^{(3)}$. Moreover, alternating direction of the z-directional $3^{rd}$ order local dipole is not canceled but purely added to achieve extremely large effective nonlinear polarization. This is because of the equi-potential surface vector which is used to average the local nonlinear dipoles having alternating directions and makes the integration, $$X_{eff\,11}^{(3)} \approx X_{33}^{(3)} \frac{1}{l_z} \int \hat{z} \cdot S_{x,3/4} m_x^3 (S_x \cdot \hat{z})^3 da,$$

purely piled up.

For the effective $2^{nd}$ order nonlinear susceptibility $X_{eff\,11}^{(2)}$ component becomes $$X_{eff\,11}^{(2)} \approx X_{33}^{(2)} \frac{1}{l_z} \int \hat{z} \cdot S_{x,\frac{3}{4}} m_x^2 (S_x \cdot \hat{z}) da = X_{33}^{(2)} \frac{1}{l_z} m_x^2 \int \hat{z} \cdot S_{x,\frac{3}{4}} da,$$

and since $\hat{z}\cdot S_{x,3/4}$ has an alternating sign along the integration path, $X_{eff\,11}^{(2)}$ vanishes. In this case, the enhanced effective nonlinear susceptibility can be obtained by alternating the polarity of a filling dielectric, and, thus, it is possible to obtain the effective nonlinear susceptibility, $$X_{eff\,11}^{(2)} \approx \frac{1}{16}\left(\frac{a}{g}\right)^3 X_{33}^{(2)}.$$

The enhancement based on the space-filling of a nonlinear electric dipole moment not only increases the nonlinear signal but also exceeds the practical limit of the magnitude of the nonlinear signal caused by laser-induced damage. Most of optical nonlinearity enhancing structures confine the electric (or magnetic) field to small volumes. Therefore, while a nonlinear signal emitting a small field confinement region suffers from the laser induced damage, most of the rest region barely emits the nonlinear signal. For this reason, the maximum achievable nonlinear signal magnitude of the structured material is not as much as $x^{NL}$ enhancement compared with those in natural materials. On the other hand, the field confinement region of the proposed structure is approximately half of the entire volume. Specifically, the additional enhancement factor, $$\frac{a}{g},$$

arises from the space-filling of a dipole moment effectively and increases the magnitude of the nonlinear signal. This is because it does not decrease the damage threshold, which is unusual in structured medium.

Since the space-filling of local nonlinear dipoles does not depend on the frequency, the extreme enhancement of effective nonlinear susceptibility can be realized in infrared and visible frequency range. However, the degree of enhancement is restricted by several practical and fundamental conditions which are reflected in the analytic model in consideration of the finite permittivity of the metal. First, the magnitude of the metal permittivity becomes smaller at higher frequencies. Therefore, the metal patches with small dielectric gap cannot support extreme confinement of an electric field, so the aspect ratio $$\frac{a}{g}$$

is limited to avoid the penetration of the electric field into the metal patches which cause optical loss. Second, the lateral unit cell length a of the mesoscopic crystal should be smaller since the wavelength become shorter for higher frequencies, and since the lateral unit cell length a is limited to around 100 nm, there is a limitation on the increase in aspect ratio. Nevertheless, in the mesoscopic crystal structure of the present disclosure, the enhancement of the effective $3^{rd}$ order electric susceptibility $x^{(3)}$ was maintained in a broad frequency range, and for the aspect ratio of 50, the enhancement of $x^{(3)}$ is 100 or more at a communication wavelength (1.55 μm)

Although the effective $x^{(3)}$ of the mesoscopic crystal well describes the $3^{rd}$ order nonlinear optical property, the conversion efficiency between a fundamental wave and a $3^{rd}$ harmonic generator may be more practically important. The mesoscopic crystal not only enhances nonlinear susceptibility, but also magnifies linear susceptibility. The magnified linear susceptibility may be desired for other applications, but it can be a constraint for maximizing the conversion efficiency due to the wave impedance mismatch between the free space and the mesoscopic crystal. Thus, the wave impedance matching layer can be used to maximize the conversion efficiency. That is, three layers composed of an upper dielectric layer, a mesoscopic crystal structure layer, and a lower dielectric layer may be formed to solve an impedance mismatch. A reflective layer may be further provided under the lower dielectric layer. The thickness of the upper and lower dielectric layers is optimized by using the nonlinear transfer matrix method. The thickness of the upper and lower dielectric layers is determined depending on the material of the mesoscopic crystal structure and the unit cell size. However, the thickness of the dielectric layers cannot perfectly match for every frequency. From the experiments, FWHM of 1 THz for the enhancement with the magnitude of $10^6$ was achieved and FWHM of 10 THz for the enhancement with the magnitude of $10^4$ was achieved.

Figure 27:
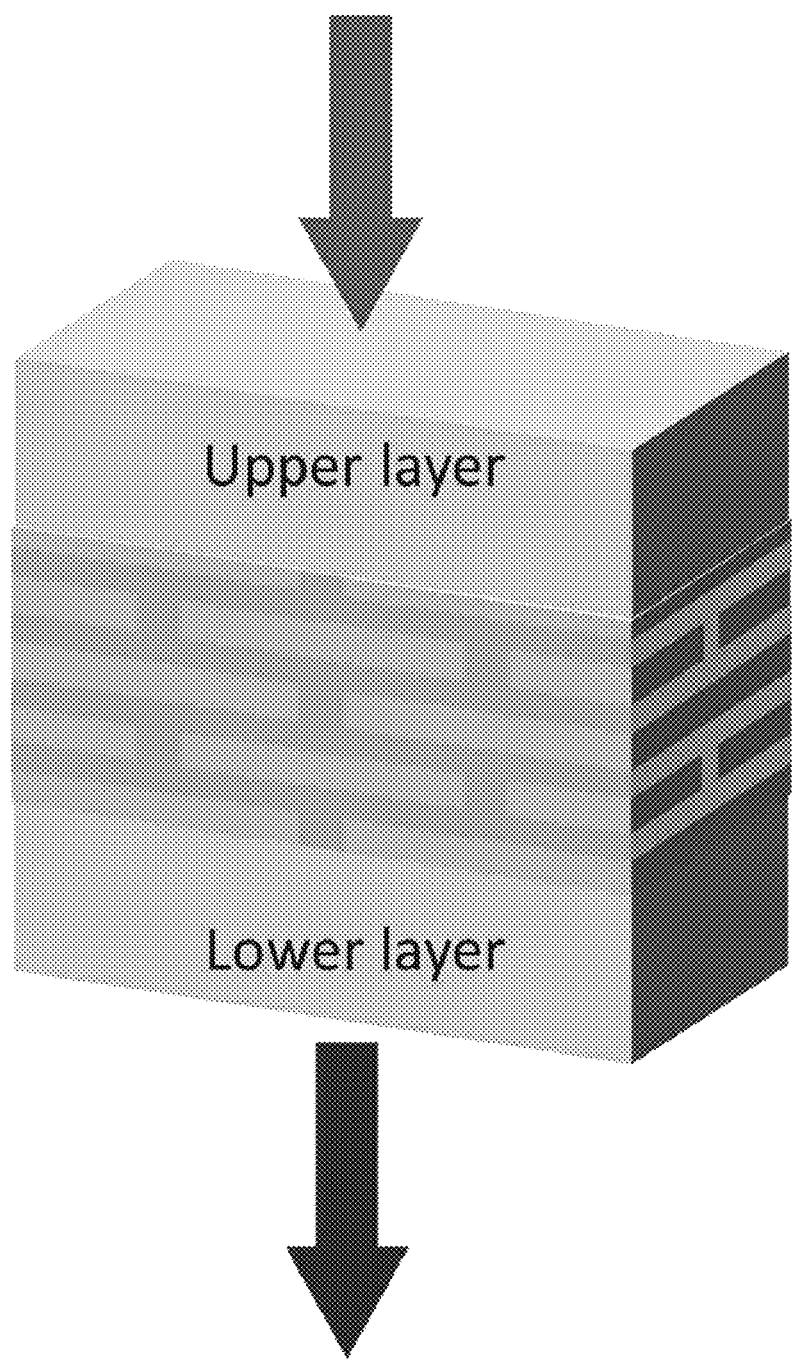
FIG. 27 is a diagram provided to explain a transmissive nonlinear optical device using a mesoscopic crystal structure according to the present disclosure.

FIG. 27 is a diagram provided to explain a transmissive nonlinear optical device using a mesoscopic crystal structure according to the present disclosure.

The mesoscopic crystal structure greatly increases the optical nonlinearity of a filling dielectric having a nonlinear property and thus can be used for nonlinear optical devices ($2^{nd}$ order harmonic wave generation, $3^{rd}$ order harmonic wave generation, sum-frequency generation, difference frequency generation, 4-wave mixing, etc.). In this case, since the wave impedance of the mesoscopic crystal is very small, an upper layer or a lower layer may be used as an impedance matching layer for efficient wavelength conversion, and the upper layer and the lower layer may be dielectric such as typical silica or may have a mesoscopic crystal structure having a different aspect ratio from the mesoscopic crystal structure between the upper layer and the lower layer.

Figure 28:
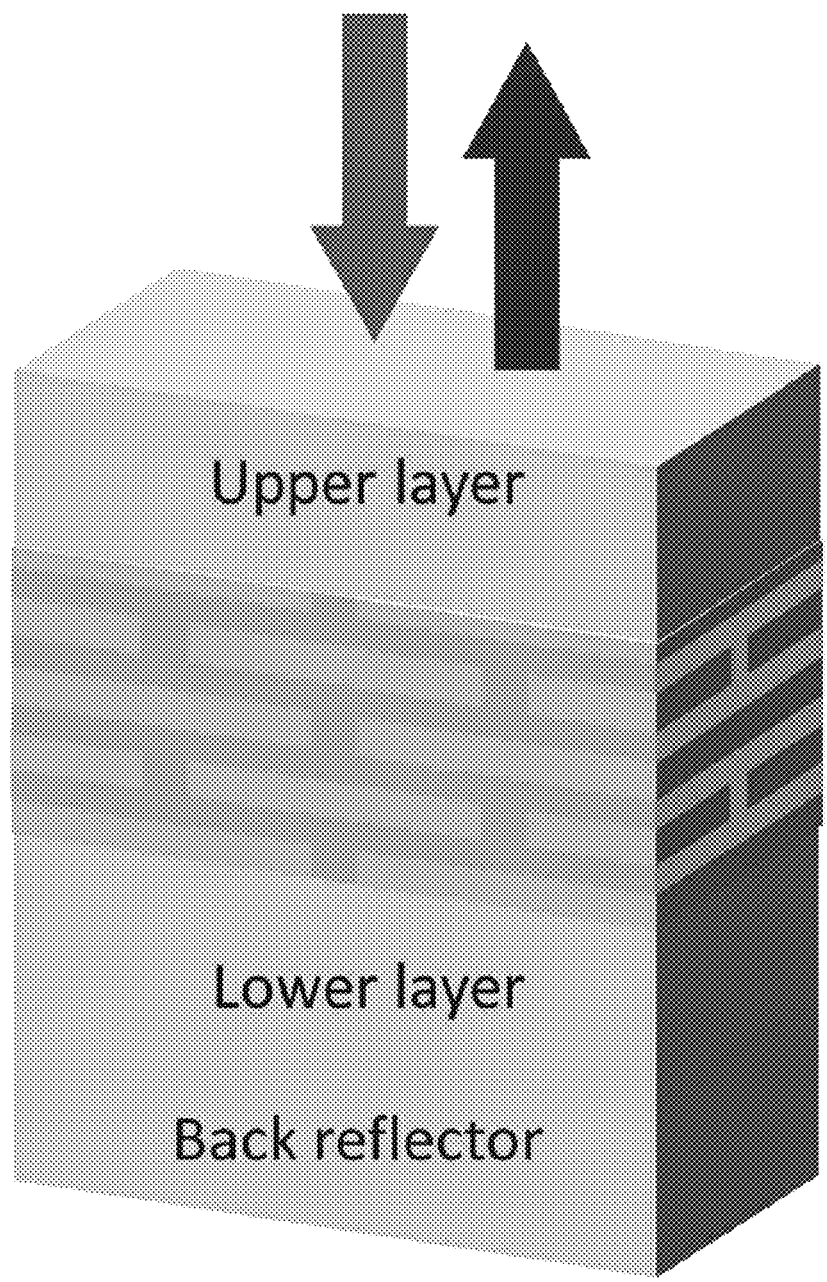
FIG. 28 is a diagram provided to explain a reflective nonlinear optical device using a mesoscopic crystal structure according to the present disclosure.

FIG. 28 is a diagram provided to explain a reflective nonlinear optical device using a mesoscopic crystal structure according to the present disclosure.

A reflective nonlinear optical device can be fabricated by placing a back reflector at the bottom of the above-described structure including the upper layer—the mesoscopic crystal structure—the lower layer (applicable to $2^{nd}$ order harmonic wave generation, $3^{rd}$ order harmonic wave generation, sum-frequency generation, difference frequency generation, 4-wave mixing, etc.). The reflective nonlinear optical device has an advantage of being able to increase the amplitude of an input wave by constructive interference of a reflective wave and an incident wave using the ack reflector. Even in this case, the components, the structure, and the thickness of the upper layer and the lower layer can be optimized to maximize the conversion efficiency in consideration of the ack reflector as well.

Figure 29:
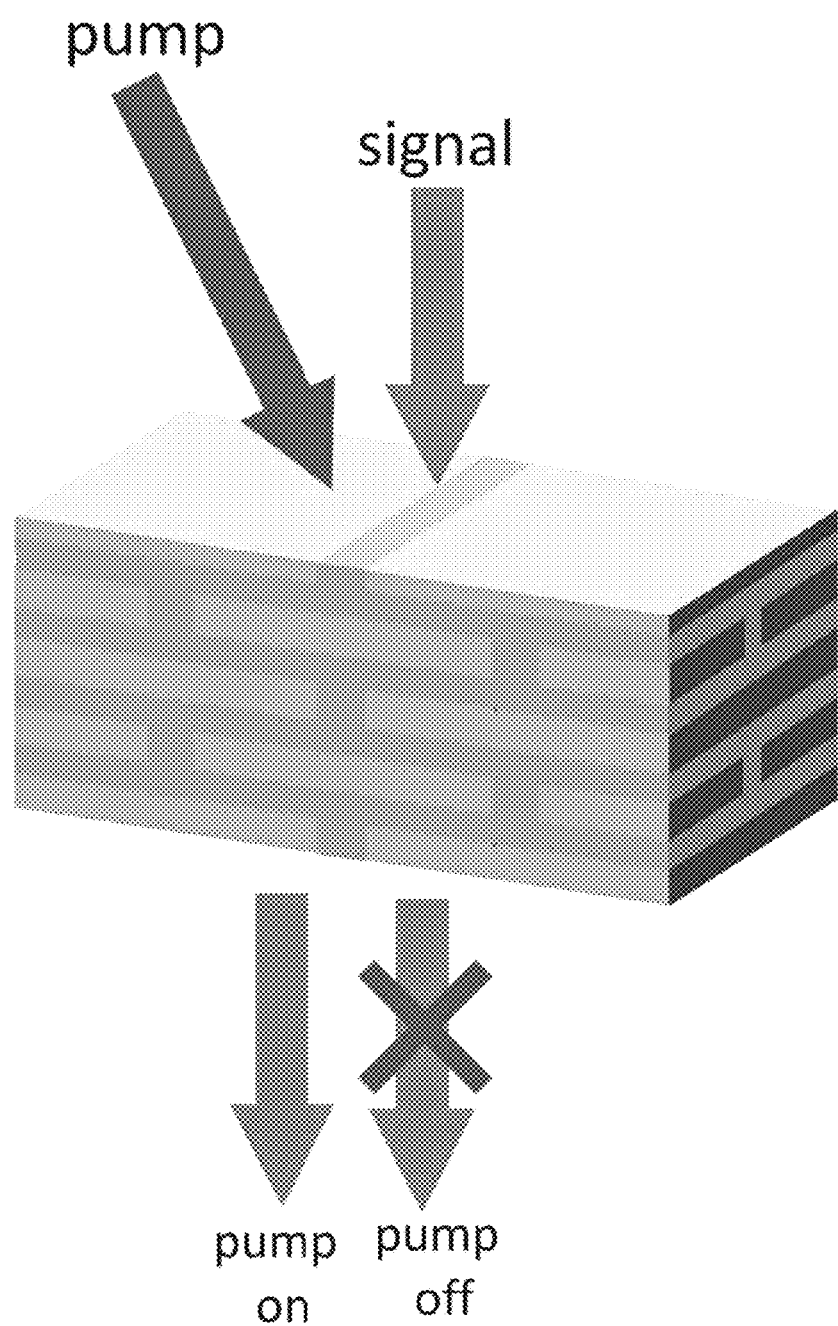
FIG. 29 is a diagram provided to explain an optical modulator using a mesoscopic crystal structure according to the present disclosure.

FIG. 29 is a diagram provided to explain an optical modulator using a mesoscopic crystal structure according to the present disclosure.

If there is a strong pump wave, the refractive index of a material with Kerr nonlinearity is changed. If this material is used as a filling dielectric, the refractive index of the mesoscopic crystal structure may be changed by light. Since the refractive index of the mesoscopic crystal structure has a very high value, a Fabry-Perot resonance becomes sharp and the refractive index is greatly changed by the Kerr nonlinearity, and, thus, it is possible to implement an all-optical modulator which is smaller in size and can operate with a smaller pump power compared with any conventional one.

The examples of the present disclosure can be implemented not only by the above-described device and/or method but also by a program not only by a program for realizing a function corresponding to the configuration of the examples of the present disclosure or a storage medium in which the program is recorded. Further, the implementation can be easily achieved by an expert in the art with reference to the above descriptions of the examples.

While the configuration of the present disclosure has been described in detail, it should be understood by a person with ordinary skill in the art that various modifications and changes may be made therein without departing from the scope of the present disclosure. Therefore, the scope of the present disclosure is not limited to the examples described above but should be defined by the following claims.

We claim:

1. A wideband ultra-high refractive index mesoscopic crystal structure using space-filling of an electric dipole, comprising:
 a first layer in which a plurality of high-conductivity unit bodies is arranged in a matrix form, and a low-conductivity material is disposed between the high-conductivity unit bodies to insulate the high-conductivity unit bodies from each other;
 a second layer in which a plurality of high-conductivity unit bodies is arranged in a matrix form, and a low-conductivity material is disposed between the high-conductivity unit bodies to insulate the high-conductivity unit bodies from each other;

a first shield layer existing between the first and second layers and made of a low-conductivity material; and a second shield layer made of a low-conductivity material and disposed on a side of the second layer such that the second layer is disposed between the first shield layer and the second shield layer, wherein, the high-conductivity unit bodies in the first layer overlap the plurality of high-conductivity unit bodies arranged in the second layer, and wherein the first layer, the first shield layer, the second layer, and the second shield layer are sequentially stacked one or more times.

2. The wideband ultra-high refractive index mesoscopic crystal structure using space-filling of an electric dipole of claim 1, wherein the low-conductivity material includes at least one of silicon dioxide, silicon, polytetrafluoroethylenes, polydimethylsiloxanes, acrylites, zinc oxide, aluminum oxide, and silver oxide.

3. The wideband ultra-high refractive index mesoscopic crystal structure using space-filling of an electric dipole of claim 1, wherein the high-conductivity unit bodies include at least one of Al, Ag, Au, Pt, Pd, Cu, Zn, Ti, Fe, Cr, Ni, Mg, Na, K, Ir, Os, W, Re, Ru, and Rh.

4. The wideband ultra-high refractive index mesoscopic crystal structure using space-filling of an electric dipole of claim 1, wherein, the high-conductivity unit bodies have a rectangular hexahedral shape, and wherein each of the high-conductivity unit bodies in the first layer overlaps four of the high-conductivity unit bodies arranged in the second layer, and wherein the center of each of the high-conductivity unit bodies in the first layer is at converging apexes of the four high-conductivity unit bodies.

5. The wideband ultra-high refractive index mesoscopic crystal structure using space-filling of an electric dipole of claim 1, wherein, the high-conductivity unit bodies have a hexagonal column shape, and wherein each of the high-conductivity unit bodies in the first layer overlaps three of the high-conductivity unit bodies arranged in the second layer, and wherein the center of the each high-conductivity unit body in the first layer is at converging apexes of the three high-conductivity unit bodies.

6. The wideband ultra-high refractive index mesoscopic crystal structure using space-filling of an electric dipole of claim 1, wherein the shield layer includes an illuminant.

7. An electromagnetic wave-absorbing device, which absorbs an electromagnetic wave using the mesoscopic crystal structure of claim 1.

8. An electro-optical modulator, comprising:
the mesoscopic crystal structure of claim 1; and
a direct current power supply configured to apply a direct electric field to the mesoscopic crystal structure.

9. A refractive index sensor using the mesoscopic crystal structure of claim 1, wherein the low-conductivity material included in the mesoscopic crystal structure is a fluid, and wherein a refractive index of the low-conductivity material is calculated by measuring a refractive index of the mesoscopic crystal structure.

10. An antigen sensor, comprising:
the mesoscopic crystal structure of claim 1; and
an antibody, wherein, the low-conductivity material in the mesoscopic crystal structure is a fluid, and wherein the antibody is attached to surfaces of the high-conductivity unit bodies in the mesoscopic crystal structure, and wherein a density of the antibody is calculated by measuring whether the antibody is bonded to an antigen.

11. A graded index lens using the mesoscopic crystal structure of claim 1, wherein a refractive index is determined depending on a position of an overlap portion between the high-conductivity unit bodies in the first layer and the high-conductivity unit bodies in the second layer on the mesoscopic crystal structure.

12. A refractive index-grating device, comprising the mesoscopic crystal structure of claim 1, wherein the high-conductivity unit bodies in the first layer in the mesoscopic crystal structure are different in width from the high-conductivity unit bodies in the second layer, and they periodically overlap each other, which causes a periodic change in refractive index.

13. The wideband ultra-high refractive index mesoscopic crystal structure using space-filling of an electric dipole of claim 1, wherein, the high-conductivity unit bodies in the mesoscopic crystal structure are made of a ferroelectric material, and wherein a polarized electromagnetic wave is incident, a wavelength of the polarized electromagnetic wave is detected according to a ferroelectric recovery of the ferroelectric material.

14. A nonlinear optical device, comprising:
a mesoscopic crystal structure of claim 1;
a third layer; and
a fourth layer, wherein
the mesoscopic crystal structure exists between the third layer and the fourth layer.

15. The nonlinear optical device of claim 14, wherein the third layer is made of vacuum, air, or a homogeneous dielectric material.

16. The nonlinear optical device of claim 14, wherein the third layer and the fourth layer have a mesoscopic crystal structure which is different in aspect ratio from the mesoscopic crystal structure.

17. The nonlinear optical device of claim 14, further comprising:
a metallic reflective layer.

18. The nonlinear optical device of claim 14, wherein at least one of the first layer, the first shield layer, the second layer, and the second shield layer has optical nonlinearity.

19. An optical modulator, comprising a wideband ultra-high refractive index mesoscopic crystal structure of claim 1, wherein
at least one of the first layer, the first shield layer, the second layer, and the second shield layer has optical nonlinearity; and
wherein the optical modulator operates using a refractive index that varies depending on an intensity of an electromagnetic field applied thereto.

* * * * *